(12) United States Patent
Kurt-Jones et al.

(10) Patent No.: US 7,388,080 B2
(45) Date of Patent: Jun. 17, 2008

(54) SELECTIVE INHIBITION OF TOLL-LIKE RECEPTOR-2

(75) Inventors: Evelyn A. Kurt-Jones, Belmont, MA (US); Robert W. Finberg, Sudbury, MA (US)

(73) Assignee: University of Massachusetts, Boston, MA (US)

(*) Notice: Subject to any disclaimer, the term of this patent is extended or adjusted under 35 U.S.C. 154(b) by 628 days.

(21) Appl. No.: 10/923,280

(22) Filed: Aug. 20, 2004

(65) Prior Publication Data

US 2005/0074823 A1   Apr. 7, 2005

Related U.S. Application Data

(60) Provisional application No. 60/496,623, filed on Aug. 20, 2003.

(51) Int. Cl.
*C07K 16/00* (2006.01)
*C07K 16/18* (2006.01)
*C12P 21/08* (2006.01)

(52) U.S. Cl. .................. 530/388.1; 530/388.2; 530/388.22; 530/389.1; 435/326

(58) Field of Classification Search ............ None
See application file for complete search history.

(56) References Cited

U.S. PATENT DOCUMENTS 5,641,638 A   6/1997 Bredt et al.

OTHER PUBLICATIONS

Buhring et al, Hybridoma, 1991, vol. 10, pp. 77-78.*
Immunobiology, The Immune System in Health and Disease, Third Edition, Janeway and Travers, Ed., 1997.*
Akira et al., "Toll-like receptors: critical proteins linking innate and acquired immunity," Nat. Immunol. 2(8):675-80 (2001).
Alexopoulou et al., "Hyporesponsiveness to vaccination with *Borrelia burgdorferi* OspA in humans and in TLR1- and TLR2-deficient mice," Nat. Med. 8(8):878-84 (2002).
Aliprantis et al., "Cell activation and apoptosis by bacterial lipoproteins through toll-like receptor-2," Science 285(5428):736-9 (1999).
Brightbill et al., "Host defense mechanisms triggered by microbial lipoproteins through toll-like receptors," Science 285(5428):732-6 (1999).
Buhring et al., "The monoclonal antibody 11G7 recognizes a novel differentiation antigen expressed on hemopoietic precursor cells," Hybridoma 10(1):77-88 (1991).
Echchannaoui et al., "Toll-like receptor 2-deficient mice are highly susceptible to *Streptococcus pneumoniae* meningitis because of reduced bacterial clearing and enhanced inflammation," J. Infect. Dis. 186(6):798-806 (2002).
Flo et al., "Human toll-like receptor 2 mediates monocyte activation by *Listeria monocytogenes*, but not by group B streptococci or lipopolysaccharide," J. Immunol. 164(4):2064-9 (2000).
Hoshino et al., "Cutting edge: Toll-like receptor 4 (TLR4)-deficient mice are hyporesponsive to lipopolysaccharide: evidence for TLR4 as the Lps gene product," J. Immunol. 162(7):3749-52 (1999).
Kurt-Jones et al., "Herpes simplex virus 1 interaction with Toll-like receptor 2 contributes to lethal encephalitis," Proc. Natl. Acad. Sci. USA 101(5):1315-20 (2004).

Kurt-Jones et al., "Role of toll-like receptor 2 (TLR2) in neutrophil activation: GM-CSF enhances TLR2 expression and TLR2-mediated interleukin 8 responses in neutrophils," Blood 100(5):1860-8 (2002).
Latz et al., "Lipopolysaccharide rapidly traffics to and from the Golgi apparatus with the toll-like receptor 4-MD-2-CD14 complex in a process that is distinct from the initiation of signal transduction," J. Biol Chem. 277(49):47834-43 (2002).
Lien and Ingalls, "Toll-like receptors," Crit. Care Med. 30(1 Supp):S1-S11 (2002).
Lien et al., "Toll-like receptor 2 functions as a pattern recognition receptor for diverse bacterial products," J. Biol. Chem. 274(47):33419-25 (1999).
Means et al., "Human toll-like receptors mediate cellular activation by *Mycobacterium tuberculosis*," J. Immunol. 163(7):3920-7 (1999).
Means et al., "The CD14 ligands lipoarabinomannan and lipopolysaccharide differ in their requirement for Toll-like receptors," J. Immunol. 163(12):6748-55 (1999).
Means et al., "The biology of Toll-like receptors," Cytokine & Growth Factor Rev. 11:219-232 (2000).
Meng et al., "Antagonistic antibody prevents toll-like receptor 2-driven lethal shock-like syndromes," J. Clin. Invest. 113(10):1473-81 (2004).
Muzio et al., "Toll-like receptor family and signalling pathway," Biochem. Soc. Trans. 28(5):563-6 (2000).
O'Neill, "The Toll/interleukin-1 receptor domain: a molecular switch for inflammation and host defence," Biochem. Soc. Trans. 28(5):557-62 (2000).
Poltorak et al., "Defective LPS signaling in C3H/HeJ and C57BL/10ScCr mice: mutations in Tlr4 gene," Science 282(5396):2085-8 (1998).
Sandor et al., "Importance of extra- and intracellular domains of TLR1 and TLR2 in NFkappa B signaling," J. Cell Biol. 162(6):1099-110 (2003).
Takeuchi et al., "Cutting Edge: Role of Toll-Like Receptor 1 in Mediating Immune Response to Microbial Lipoproteins," J. Immunol. 169:10-14 (2002).
Takeuchi et al., "Cutting edge: TLR2-deficient and MyD88-deficient mice are highly susceptible to *Staphylococcus aureus* infection," J. Immunol. 165(10):5392-6 (2000).
Underhill, "The Toll-like receptor 2 is recruited to macrophage phagosomes and discriminates between pathogens," Nature 401(6755):811-5 (1999).
Vanhove et al, "Selective blockade of CD28 and not CTLA-4 with a single-chain Fv-alpha1-antitrypsin fusion antibody," Blood 102(2):564-70 (2003).
Werts et al., "Leptospiral lipopolysaccharide activates cells through a TLR2-dependent mechanism," Nat. Immunol. 2(4):346-52 (2001).
Wyllie et al., "Evidence for an accessory protein function for Toll-like receptor 1 in anti-bacterial responses," J. Immunol. 165(12):7125-32 (2000).
Yoshimura et al., "Cutting Edge: Recognition of Gram-Positive Bacterial Cell Wall Components by the Innate Immune System Occurs Via Toll-Like Receptor 2," J. Immunol., 163:1-5 (1999).
* cited by examiner

*Primary Examiner*—Bridget E. Bunner
*Assistant Examiner*—Fozia M Hamud
(74) *Attorney, Agent, or Firm*—Fish & Richardson P.C.

(57) ABSTRACT

It has been found that Toll-like receptor 1 and Toll-like receptor 2 (TLR2) physically interact. Antibodies that specifically bind to TLR2 and selectively inhibit induction of cytokines are also described. The invention relates to specific antibodies that selectively bind to TLR2, and to methods of identifying compounds that selectively interfere with signaling through TLR1/TLR2 complexes.

22 Claims, 6 Drawing Sheets

Figure 2A
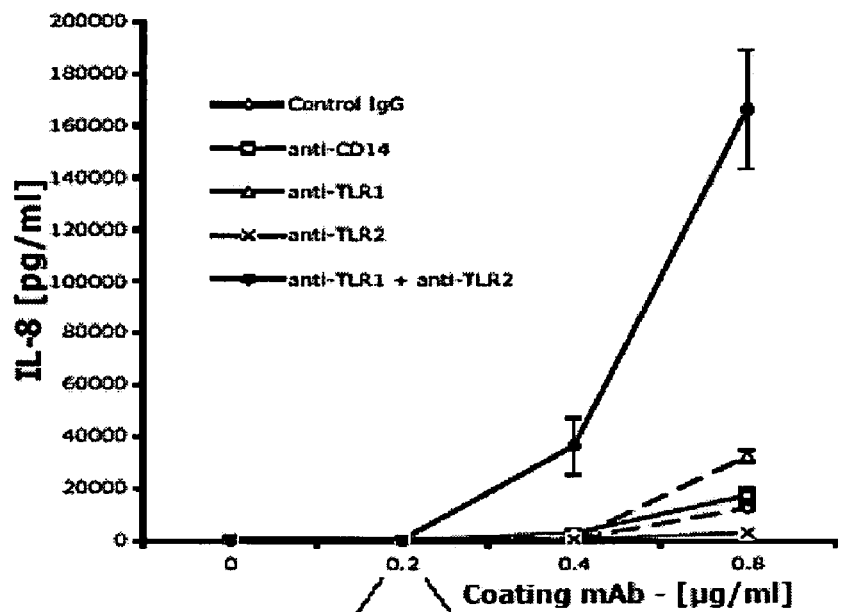
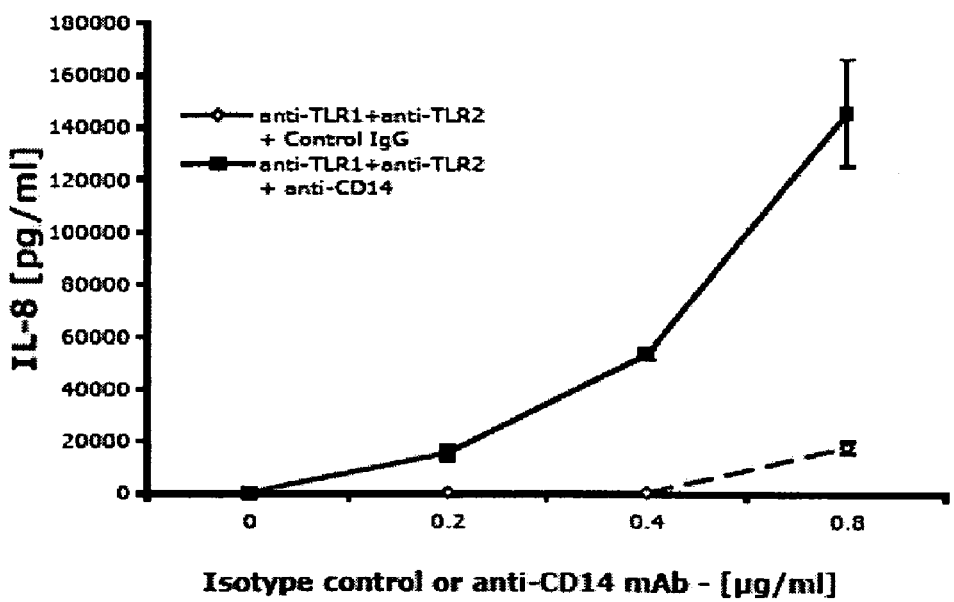
Figure 2B

SEQUENCE LISTING

```
<160> NUMBER OF SEQ ID NOS: 8

<210> SEQ ID NO 1
<211> LENGTH: 35
<212> TYPE: DNA
<213> ORGANISM: Artificial Sequence
<220> FEATURE:
<223> OTHER INFORMATION: Primer

<400> SEQUENCE: 1
gcgcctcgag tgtcacagga cagcactggt gtctg                                35

<210> SEQ ID NO 2
<211> LENGTH: 34
<212> TYPE: DNA
<213> ORGANISM: Artificial Sequence
<220> FEATURE:
<223> OTHER INFORMATION: Primer

<400> SEQUENCE: 2
cgcgggtacc ctaggacttt atcgcagctc tcag                                 34

<210> SEQ ID NO 3
<211> LENGTH: 37
<212> TYPE: DNA
<213> ORGANISM: Artificial Sequence
<220> FEATURE:
<223> OTHER INFORMATION: Primer

<400> SEQUENCE: 3
gcgcctcgag tgcaacataa ctctgctgat cgtcacc                              37

<210> SEQ ID NO 4
<211> LENGTH: 35
<212> TYPE: DNA
<213> ORGANISM: Artificial Sequence
<220> FEATURE:
<223> OTHER INFORMATION: Primer

<400> SEQUENCE: 4
cgcgggtacc ctatttcttt gcttgctctg tcagc                                35
```

```
<210> SEQ ID NO 5
<211> LENGTH: 28
<212> TYPE: DNA
<213> ORGANISM: Artificial Sequence
<220> FEATURE:
<223> OTHER INFORMATION: Primer

<400> SEQUENCE: 5
ctttcattag gatcctccag ctggtttg                                       28

<210> SEQ ID NO 6
<211> LENGTH: 38
<212> TYPE: DNA
<213> ORGANISM: Artificial Sequence
<220> FEATURE:
<223> OTHER INFORMATION: Primer

<400> SEQUENCE: 6
gcgcctcgag ttcagacatg tgaaagtcct ttagtagg                            38

<210> SEQ ID NO 7
<211> LENGTH: 30
<212> TYPE: DNA
<213> ORGANISM: Artificial Sequence
<220> FEATURE:
<223> OTHER INFORMATION: Primer

<400> SEQUENCE: 7
ctaacattga tatcagtaag aatagttttc                                     30

<210> SEQ ID NO 8
<211> LENGTH: 35
<212> TYPE: DNA
<213> ORGANISM: Artificial Sequence
<220> FEATURE:
<223> OTHER INFORMATION: Primer

<400> SEQUENCE: 8
gcgcctcgag caccgagagg cggacatcct gaacc                               35
```

US 7,388,080 B2

SELECTIVE INHIBITION OF TOLL-LIKE RECEPTOR-2

CLAIM OF PRIORITY

This application claims priority under 35 USC §119(e) to U.S. patent application Ser. No. 60/496,623, filed on Aug. 20, 2003, the entire contents of which are incorporated herein by reference.

FEDERALLY SPONSORED RESEARCH OR DEVELOPMENT

This invention was made with Government support under Grant No. RO1 GM63244 awarded by the National Institutes of Health. The Government has certain rights in the invention.

TECHNICAL FIELD

This invention relates to compounds that selectively inhibit signaling through toll-like receptor 2 (TLR2), and methods of making and using them.

BACKGROUND

The Toll-like receptor (TLR) family of proteins is an integral part of the human innate immune system (Medzhitov et al., 2000, Cytokine Growth Factor Rev., 11:219-232; Akira et al., 2001, Nat. Immunol., 2:675-680). The function of the innate immune system is thought to be the recognition of invading pathogens, the activation of inflammation to control pathogen spread and the subsequent activation of an adaptive immune response specifically directed to the elimination of the pathogen.

TLR2 recognizes a variety of microbial molecules (Lien, 1999, *J. Biol. Chem.*, 274:33419-33425; Yoshimura et al., 1999, J. Immunol., 163:1-5; Underhill et al., 1999, Nature, 401:811-815; Brightbill et al., 1999, Science, 285:732-736; Aliprantis et al., 1999, Science, 285:736-739; Means et al., 1999, J. Immunol., 163:6748-6755). For example, the TLR2 receptor participates in the recognition of Gram positive bacteria, peptidoglycan, lipopeptides, and zymosan from yeast cell walls. Also, Leptospiral LPS (lipopolysaccharide) exerts its activity in a TLR2-dependent manner (Werts et al., 2001, Nat. Immunol. 2:346-352). TLR2 is involved in recognition of viable *M. tuberculosis* as well as recognition of lipoarabinomannan from rapidly growing mycobacteria (Means et al., 1999, J. Immunol., 163:6748-6755; Means, et al., 1999, J. Immunol., 163:3920-3927). Numerous additional ligands are recognized via TLR2 (reviewed in Lien et al., 2002, Crit. Care Med., 30:S1-11). In studies of TLR1 and TLR2 knockout mice, the receptors were shown to cooperate in recognition of *B. burgdorferi* outer surface protein A lipoprotein OspA (Alexopoulou et al., 2002, Nat. Med., 8:878-884). Knockout studies have also suggested that TLR1 and TLR2 cooperate in the recognition of 19 kDa mycobacterial lipopeptide and several synthetic triacylated lipopeptides (Takeuchi et al., 2002, J. Immunol., 169:10-14).

SUMMARY

The invention relates, in part, to the discovery of an antibody, 11G7, which specifically binds to Toll-like receptor 2 (TLR2) and can block the production of inflammatory cytokines. It also relates to the discovery that TLR2-mediated induction of cytokines by ara-lipoarabinomannan (araLAM) or lipopeptide N-palmitoylglyceryl Cys-Ser-(Lys)4 ($Pam_3CSK_4$) can be selectively inhibited. The invention includes compounds that selectively inhibit cytokine induction by interacting with TLR2 and methods of identifying and using such compounds. It has also been found that the physical interaction between both intracellular and extracellular domains of TLR1 and TLR2 is required for induction of cytokines by these two receptors. Also included in the invention are assays for identifying compounds that interfere with signaling through TLR1/TLR2 complexes (referred to herein as "TLR1/TLR2"), but do not affect signaling through TLR2/TLR6 complexes (referred to herein as "TLR2/TLR6"), and methods of using such compounds. As used herein, "signaling through TLR1/TLR2" refers to the induction of cytokine expression in response to binding of a ligand, e.g., araLAM or $Pam_3CSK_4$, to TLR1/TLR2. As used herein, "signaling through TLR2/TLR6" refers to the induction of cytokine expression in response to binding of a ligand, e.g., zymosan, to TLR2/TLR6.

In one aspect, the invention relates to antibodies and antigen-binding fragments thereof that specifically bind to the extracellular domain of Toll-like receptor-2 protein (TLR2) that can block the induction of cytokine production by human peripheral blood mononuclear cells (PBMCs) stimulated with ara-lipoarabinomannan (araLAM) (mediated by signaling through TLR1/TLR2 complexes), but do not significantly inhibit the induction of cytokine production by peripheral blood mononuclear cells (PMBCs) stimulated with zymosan (mediated by signaling through TLR2/TLR6 complexes).

The antibody can be a monoclonal antibody. The antibody can also be a chimeric antibody, a recombinant antibody, a humanized antibody, a single-chain antibody, or an antibody fragment. Included in the invention is a cell line that produces an antibody or an antibody that can be manipulated to produce an antibody product (e.g., an antibody fragment) as described herein.

In some embodiments, the antibody or antigen-binding fragment thereof is an 11G7 antibody or antigen-binding fragment thereof, e.g., an Fab fragment or a single chain antibody. Also included is a hybridoma cell line that produces the 11G7 antibody, e.g., the 11G7 hybridoma deposited at American Type Culture Collection (ATCC) and designated PTA-5014. In some embodiments, the invention includes chimeric 11G7 antibodies and cell lines that produce the chimeric 11G7 antibodies, as well as humanized 11G7 antibodies and cell lines that produce the humanized 11G7 antibody.

In some embodiments, the antibody or antigen-binding fragment thereof is produced by a hybridoma cell line deposited with the American Type Culture Collection under deposit no. PAT-5014, or selectively binds (e.g., competitively binds, or binds to same epitope, e.g., a conformational or a linear epitope) to an antigen that is selectively bound by an antibody produced by a hybridoma cell line deposited with the American Type Culture Collection under deposit no. PAT-5014.

In some embodiments, the antibody or antigen-binding fragment thereof is produced by immunizing an animal with a cell expressing TLR2.

In another embodiment, the invention relates to methods for inhibiting TLR2 activation in a cell. The method includes contacting the cell with an anti-TLR2 antibody or antigen-binding fragment thereof, as described herein that specifically binds to TLR2 (e.g., to the extracellular domain), e.g., an antibody or antigen-binding fragment thereof that can block cytokine production by PMBCs stimulated with araLAM, but does not block cytokine production stimulated by zymosan (e.g., an 11G7 antibody or antigen-binding fragment thereof).

In another aspect, the invention relates to pharmaceutical compositions including an antibody or antigen-binding fragment thereof, as described herein. In some embodiments, the invention relates to a method of decreasing inflammation in a subject by administering a therapeutically effective amount of the pharmaceutical composition. Also included is a diagnostic reagent that includes an antibody as described herein or antigen-binding fragment thereof that specifically binds to TLR2.

In another aspect, the invention relates to methods of identifying candidate compounds that specifically block cytokine production by human peripheral blood mononuclear cells (PBMCs) stimulated with ara-lipoarabinomannan (araLAM), but do not block cytokine production by PMBCs stimulated with zymosan, the method comprising:
a. obtaining a first sample comprising TLR1 and TLR2;
b. contacting the sample with a test compound;
c. identifying a test compound that blocks one or both of:
  i. formation of TLR1/TLR2 complexes in the first sample; or
  ii. binding of araLAM to TLR1/TLR2 complexes in the first sample;
d. obtaining a second sample comprising TLR2 and TLR6;
e. contacting the second sample with the test compound identified in step (c); and
f. identifying a test compound that does not significantly block one or more of:
  i. formation of TLR2/TLR6 complexes in the first sample; or
  ii. binding of zymosan to TLR2/TLR6 complexes in the first sample.

Test compounds identified in step f are candidate compounds that specifically blocks cytokine production by human peripheral blood mononuclear cells (PBMCs) stimulated with ara-lipoarabinomannan (araLAM), but does not block cytokine production by PMBCs stimulated with zymosan.

Further, the invention relates to compounds that specifically bind to the extracellular domain of Toll-like receptor-2 protein (TLR2) that can block the induction of cytokine production by human peripheral blood mononuclear cells (PBMCs) stimulated with ara-lipoarabinomannan (araLAM) (mediated by signaling through TLR1/TLR2 complexes), but do not significantly inhibit the induction of cytokine production by peripheral blood mononuclear cells (PBMCs) stimulated with zymosan (mediated by signaling through TLR2/TLR6 complexes).

As used herein, a molecule that "specifically binds" to a target is a molecule that binds to a particular target, e.g., a TLR2 polypeptide, but which does not substantially recognize or bind to other molecules in a sample, e.g., a biological sample, which includes the target, e.g., a TLR2 polypeptide. An "11G7" antibody is a monoclonal antibody produced by the 11G7 hybridoma cell line, as described herein.

As used herein, the "extracellular domain of TLR2" is amino acids 1-589 of the human polypeptide (GeneID: 7097; UniGene Cluster Hs.519033; NCBI Accession #AAH33756, AAM23001, AAC34133), or the corresponding region of a polypeptide from another species.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Other features and advantages of the invention will be apparent from the detailed description, drawings, and from the claims.

DESCRIPTION OF DRAWINGS

FIG. 2A is a graph depicting the results of experiments in which the level of IL-8 expression (pg/ml) was assayed in the presence of varying concentrations of control antibody (OKT8), anti-CD14 (26ic), anti-TLR1 (GD2.F4), anti-TLR2 (TL2.1), and both anti-TLR1 and anti-TLR2.

FIG. 2B is a graph depicting the results of experiments in which the level of IL-8 expression was assayed in the presence of anti-TLR1 (GD2.F4), anti-TLR2 (TL2.1), and control IgG or anti-TLR1, anti-TLR2, and anti-CD14 monoclonal antibodies. TLR1 and TLR2 antibodies were provided at 0.2 μg/ml. Varying concentrations of isotype control or anti-CD14 antibodies were used.

μg/ml), and NF-κB luciferase reporter gene activity was measured. IL-1β was used as a positive control.

Figure 5A:
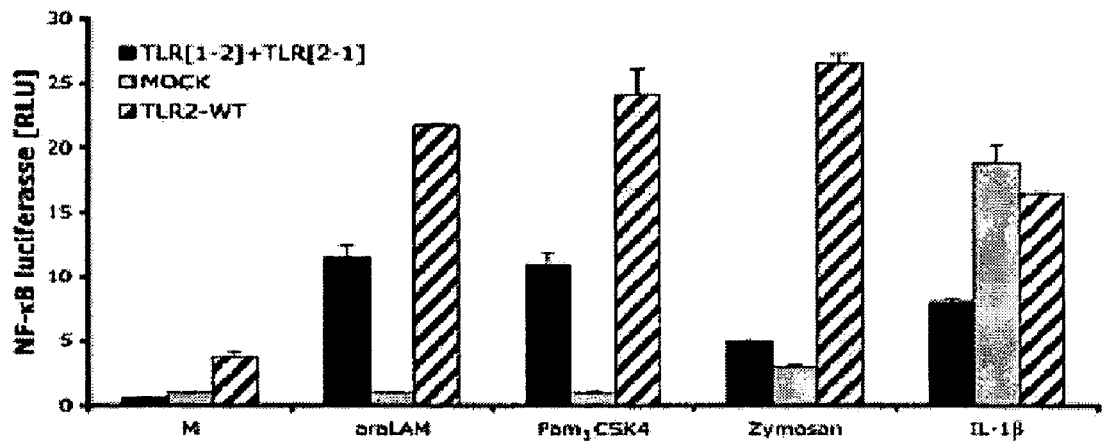
FIG. 5A is a bar graph depicting the results of experiments in which HEK293-CD14 cells were co-transfected with TLR [1-2] and TLR [2-1] DNA encoding chimeric proteins or with wild type TLR2 DNA. Cells were induced with araLAM (1 μg/ml), lipopeptide N-palmitoylglyceryl ($Pam_3$) Cys-Ser-(Lys)4 ($Pam_3CSK_4$)(100 ng/ml) or zymosan (10
Figure 5B:
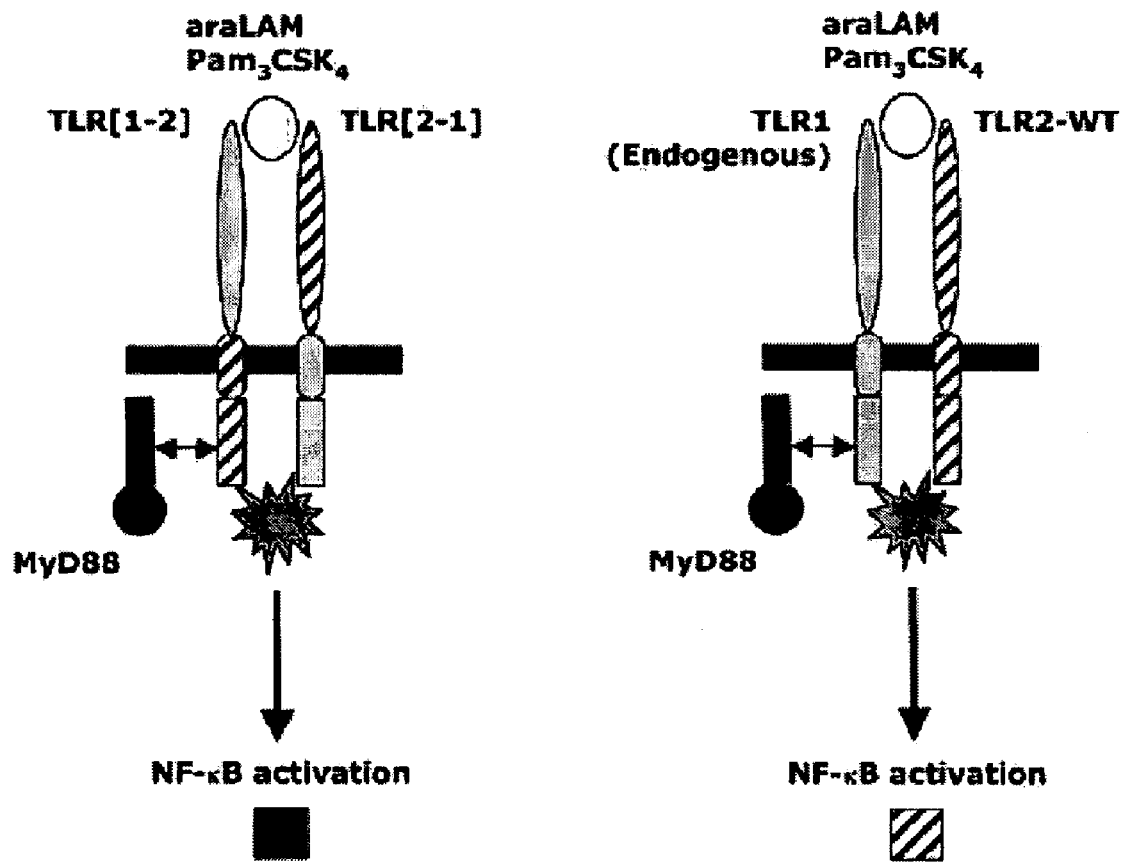

FIG. 5B is a schematic model of co-transfection of TLR [1-2] and TLR [2-1] chimeric proteins.

Figure 6A:
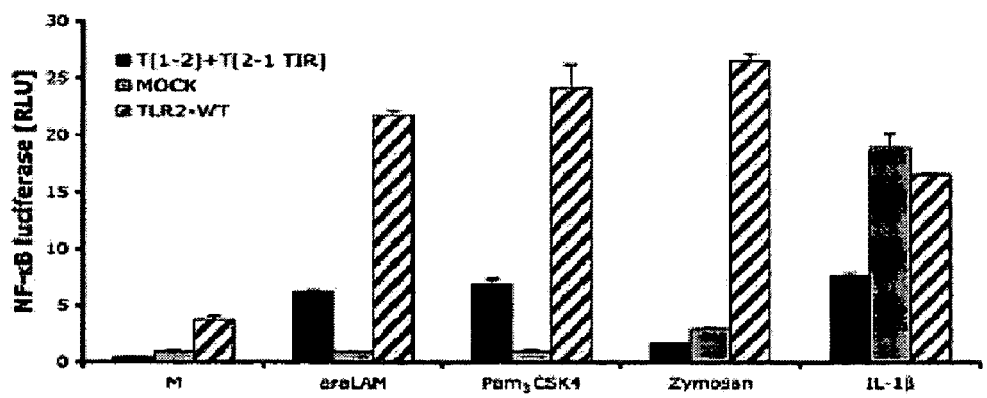

FIG. 6A is a bar graph depicting the results of experiments in which HEK293-CD14 cells were co-transfected with TLR [1-2] and TLR [2-1 TIR] DNA encoding chimeric proteins or with wild type TLR2 DNA and stimulated for six hours with araLAM (1 μg/ml), $Pam_3CSK_4$ (100 ng/ml) or zymosan (10 pg/ml), the cells were lysed and NF-κB luciferase reporter gene activity was measured. IL-1β was used as a positive control.

Figure 6B:
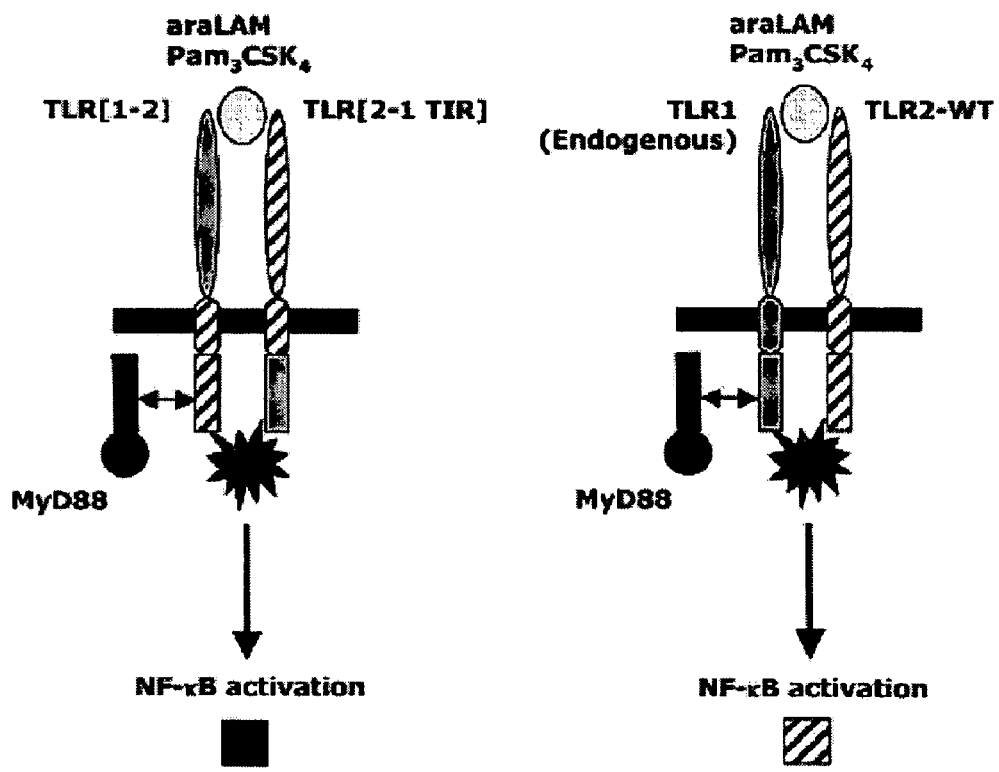

FIG. 6B is a schematic model of co-transfection of TLR [1-2] and TLR [2-1 TIR] chimeric proteins.

DETAILED DESCRIPTION

The Toll-like receptors (TLRs) are believed to play an important role in the induction of inflammatory cytokines in response to pathogens including bacteria and viruses, a response which in some cases can be detrimental to the host (Kurt-Jones et al., 2004, Proc. Net. Acad. Sci. USA, 101(5): 1315-1320). For example, signaling through TLR2 is associated with lethal viral encephalitis in HSV-1 infection (Id.). However, complete inhibition of TLR2-mediated signaling may not be desirable, as knockout animal studies have shown that TLR2-deficient mice are highly susceptible to *Streptococcus pneumoniae* meningitis (Echchannaoui et al., 2002, J. Infect. Dis., 186(6):798-806) and to *Staphylococcus aureus* infection (Takeuchi et al., 2000, J. Immunol., 165 (10):5392-6). In particular, the lethal viral encephalitis associated with TLR2-mediated signaling in HSV-1 infection does not appear to be mediated by TLR2/TLR6 signaling, so is likely to be due to TLR1/TLR2 mediated signaling. Thus, agents that block some, but not all, TLR2-mediated signaling are desirable for treating detrimental inflammatory response. e.g., to gram positive bacteria, without destroying the immune response entirely.

It is demonstrated herein that an antibody that specifically binds to TLR2 (i.e., does not bind to a significant extent to other molecules, i.e., other TLRs) is useful for selectively inhibiting TLR2-mediated induction of cytokine expression. Accordingly, antibodies and other molecules or compounds that specifically bind to TLR2 are useful as reagents for, e.g., modulation of activity induced by TLR2 such as cytokine activity. Furthermore, antibodies and other molecules or compounds that specifically bind to TLR2 and block induction of cytokines by araLAM, but not by zymosan, are useful for selective induction of cytokines. Antibodies having these properties can be used, e.g., as commercial reagents for studies of pathways related to TLR2 function, as diagnostic tools, and as compounds for treating disorders associated with TLR2 (e.g., by decreasing undesirable activation of the innate immune system, e.g., inflammation). Compounds that selectively interfere with signaling through TLR1/TLR2 complexes (e.g., an anti-TLR2 antibody, e.g., 11G7) are also useful for treating conditions in which a subject exhibits an undesired activation of the innate immune system associated with signaling through TLR1/TLR2 complexes.

Furthermore, it is shown herein that optimal activation of cytokine secretion by TLRs involves TLR1 and TLR2 receptor clustering with CD14 acting as an accessory protein on the cell surface. Monoclonal antibody blocking was used to demonstrate that both TLR1 and TLR2 are required for extracellular recognition of araLAM. This was confirmed by experiments involving transfection of cells with dominant negative mutants of either TLR1 or TLR2. Antibody cross-linking studies demonstrated that aggregation of TLR1 and TLR2 into the same domain was sufficient to induce signal transduction events independently of ligand recognition. Transfection of cells with labeled TLRs demonstrated the surprising finding that TLR1 and TLR2 are associated even before ligand stimulation or cross-linking. Using confocal microscopy to detect labeled TLR1 and TLR2, it was discovered that both receptors are expressed on the surface of dual-receptor transfected cells and are in close association without ligand or antibody cross-linking.

A similar co-localization pattern was observed in several cell clones expressing fluorescent protein labeled TLR1 and TLR2 receptors. TLR1 and TLR2 receptors were found to be present in a pre-assembled complex, and to be transported as pre-assembled complexes to the cell membrane. This interaction was independent of ligand binding. These data suggest that these receptors heterocomplexize prior to expression on the cell surface.

The data described herein demonstrate a physical interaction between TLR1 and TLR2. Thus, compounds that disrupt the physical interaction between TLR1 and TLR2, or prevent binding of ligands to the TLR1/TLR2 complex can be used to inhibit cytokine expression. The identification of an agent (e.g., an anti-TLR2 antibody as described herein, e.g., 11G7) that can selectively inhibit cytokine expression mediated by TLR1/TLR2 demonstrates that it is possible to selectively inhibit such expression.

Deposit of TLR2 Antibody 11G7

The invention includes a novel hybrid continuous cell line that produces a novel monoclonal antibody, termed "11G7" (ATCC accession No. PTA-5014), that is directed to an epitope on the extracellular surface of TLR2. By binding to TLR2, 11G7 can selectively block the activation of TLR2, e.g., by araLAM, thus inhibiting the production of inflammatory cytokines. The invention includes antibodies that specifically bind to TLR2 and selectively inhibit cytokine expression induced by araLAM. Such antibodies include 11G7 antibodies as well as variants of 11G7 such as recombinant antibodies, chimeric antibodies, humanized antibodies, or antibody fragments.

Under the terms of the Budapest Treaty on the International Recognition of the Deposit of Microorganisms for the Purpose of Patent Procedure, deposit of the following materials has been made with the American Type Culture Collection (ATCC) of Rockville, Md., USA.

Applicants and applicants' assignee, University of Massachusetts, represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 C.F.R. 1.14 and 35 U.S.C. § 122. The deposited material will be maintained with all the care necessary to keep it viable and uncontaminated for a period of at least five years after the most recent request for the furnishing of a sample of the deposited plasmid, and in any case for a period of at least thirty (30) years after the date of deposit or for the enforceable life of the patent, whichever period is longer. Applicants' assignee acknowledges its duty to replace the deposit should the depository be unable to replace the deposit should the depository be unable to furnish a sample when requested due to the condition of the deposit.

11G7 (described herein) was deposited on Feb. 21, 2003, with the American Type Culture Collection (Rockville, Md.) and has received ATCC designation PTA-5014.

Antibodies

The antibodies and antigen-binding fragments thereof described herein specifically bind to the extracellular domain of TLR2 and can inhibit the induction of cytokine activity in a cell that has been induced by araLAM, but do not inhibit induction of cytokine activity by zymosan. In some embodiments, the antibody or antigen-binding fragment thereof is 11G7 or an antigen-binding fragment thereof.

In some embodiments, the antibody or antigen-binding fragment thereof or selectively binds (e.g., competitively binds, or binds to same epitope, e.g., a conformational or a linear epitope) to an antigen that is selectively bound by an antibody produced by a hybridoma cell line deposited with the American Type Culture Collection under deposit no. PAT-5014. Thus, the epitope can be in close proximity spatially or functionally-associated, e.g., an overlapping or adjacent epitope in linear sequence or conformational space, to the one recognized by the 11G7 antibody. Potential epitopes can be identified computationally using a peptide threading program, and verified using methods known in the art, e.g., by assaying binding of the 11G7 antibody to mutants or fragments of the TLR2, e.g., mutants or fragments of the extracellular domain.

Methods of determining the sequence of an antibody described herein are known in the art; for example, the sequence of the 11G7 antibody can be determined by using known techniques to isolate and identify a cDNA encoding the 11G7 antibody from the 11G7 hybridoma described herein. Methods for determining the sequence of a cDNA are known in the art.

The antibodies described herein typically have at least one or two heavy chain variable regions (VH), and at least one or two light chain variable regions (VL). The VH and VL regions can be further subdivided into regions of hypervariability, termed complementarity determining regions (CDR), which are interspersed with more highly conserved framework regions (FR). These regions have been precisely defined (see, Kabat et al., Sequences of Proteins of Immunological Interest, Fifth Edition, U.S. Department of Health and Human Services, NIH Publication No. 91-3242, 1991 and Chothia et al., 1987, J. Mol. Biol., 196:901-917). Antibodies or antibody fragments containing one or more framework regions are also useful in the invention. Such fragments have the ability to specifically bind to the extracellular domain of TLR2 and to inhibit cytokine activity in a cell that has been induced with araLAM.

An antibody as described herein can include a heavy and/or light chain constant region (constant regions typically mediate binding between the antibody and host tissues or factors, including effector cells of the immune system and the first component (C1q) of the classical complement system), and can therefore form heavy and light immunoglobulin chains, respectively. For example, the antibody can be a tetramer (two heavy and two light immunoglobulin chains, which can be connected by, for example, disulfide bonds). The antibody can contain only a portion of a heavy chain constant region (e.g., one of the three domains heavy chain domains termed CH1, CH2, and CH3, or a portion of the light chain constant region (e.g., a portion of the region termed CL).

Antigen-binding fragments are also included in the invention. Such fragments can be: (i) a Fab fragment (i.e., a monovalent fragment consisting of the VL, VH, CL, and CH1 domains); (ii) a F(ab')2 fragment (i.e., a bivalent fragment containing two Fab fragments linked by a disulfide bond at the hinge region); (iii) a Fd fragment consisting of the VH and CH1 domains; (iv) a Fv fragment consisting of the VL and VH domains of a single arm of an antibody, (v) a dAb fragment (Ward et al., 1989, Nature, 341:544-546), which consists of a VH domain; and/or (vi) an isolated complementarity determining region (CDR).

Fragments of antibodies (including antigen-binding fragments as described above) can be synthesized using methods known in the art such as in an automated peptide synthesizer, or by expression of a full-length gene or of gene fragments in, for example, E. coli. F(ab')$_2$ fragments can be produced by pepsin digestion of an antibody molecule, e.g., 11G7, and Fab fragments can be generated by reducing the disulfide bridges of F(ab')$_2$ fragments. Alternatively, Fab expression libraries can be constructed (Huse et al., 1989, Science, 246:1275-81) to allow relatively rapid identification of monoclonal Fab fragments with the desired specificity.

Methods of making other antibodies and antibody fragments are known in the art. For example, although the two domains of the Fv fragment, VL and VH, are coded for by separate genes, they can be joined, using recombinant methods or a synthetic linker that enables them to be made as a single protein chain in which the VL and VH regions pair to form monovalent molecules (known as single chain Fv (scFv); see e.g., Bird et al., 1988, Science, 242:423-426; Huston et al., 1988, Proc. Natl. Acad. Sci. USA, 85:5879-5883; Colcher et al., 1999, Ann. NY Acad., Sci. 880:263-80; and Reiter, 1996, Clin. Cancer Res., 2:245-52).

Techniques for producing single chain antibodies are also described in U.S. Pat. Nos. 4,946,778 and 4,704,692. Such single chain antibodies are encompassed within the term "antigen-binding fragment" of an antibody. These antibody fragments are obtained using conventional techniques known to those of ordinary skill in the art, and the fragments are screened for utility in the same manner that intact antibodies are screened. Moreover, a single chain antibody can form complexes or multimers and, thereby, become a multivalent antibody having specificities for different epitopes of the same target protein.

Antibodies and portions thereof that are described herein can be monoclonal antibodies, generated from monoclonal antibodies, or can be produced by synthetic methods known in the art. Antibodies can be recombinantly produced (e.g., produced by phage display or by combinatorial methods, as described in, e.g., U.S. Pat. No. 5,223,409; WO 92/18619; WO 91/17271; WO 92/20791; WO 92/15679; WO 93/01288; WO 92/01047; WO 92/09690; WO 90/02809; Fuchs et al., 1991, Bio/Technology, 9:1370-1372; Hay et al., 1992, Human Antibody Hybridomas, 3:81-85; Huse et al., 1989, Science, 246:1275-1281; Griffiths et al., 1993, EMBO J., 12:725-734; Hawkins et al., 1992, J. Mol. Biol., 226: 889-896; Clackson et al., 1991, Nature, 352:624-628; Gram et al., 1992, Proc. Natl. Acad. Sci. USA, 89:3576-3580; Garrad et al., 1991, Bio/Technology, 9:1373-1377; Hoogenboom et al., 1991, Nucl. Acids Res., 19:4133-4137; and Barbas et al., 1991, Proc. Natl. Acad. Sci. USA, 88:7978-7982).

As one example, a TLR2 antibody can be made by immunizing an animal with a TLR2 polypeptide (including at least a portion of the extracellular domain), or fragment (e.g., an antigenic peptide fragment derived from (i.e., having the sequence of a portion of) the extracellular domain of TLR2) thereof, or a cell expressing the TLR2 antigen or an antigenic fragment thereof. In some embodiments, antibodies or antigen-binding fragments thereof described herein can bind to a purified TLR2 or TLR2 extracellular domain. In some embodiments, the antibodies or antigen-binding fragments thereof can bind to a TLR2 or TLR2 extracellular domain in a tissue section, a whole cell (living, lysed, or fractionated), or a membrane fraction. Antibodies can be tested, e.g., in in vitro systems such as peripheral blood mononuclear cells (PBMCs), for the ability to inhibit the induction of cytokine expression by araLAM and the inability to inhibit the induction of cytokine expression by zymosan.

In the event an antigenic peptide derived from TLR2 is used, it will typically include at least eight (e.g., 10, 15, 20, 30, 50, 100 or more) consecutive amino acid residues of the extracellular domain of TLR2. In some embodiments, the antigenic peptide will comprise all of the extracellular domain of TLR2. The antibodies generated can specifically bind to one of the proteins in their native form (thus, antibodies with linear or conformational epitopes are within the invention), in a denatured or otherwise non-native form, or both. Peptides likely to be antigenic can be identified by methods known in the art, e.g., by computer-based antigenicity-predicting algorithims. Conformational epitopes can sometimes be identified by identifying antibodies that bind to a protein in its native form, but not in a denatured form.

The host animal (e.g., a rabbit, mouse, guinea pig, or rat) can be immunized with the antigen, optionally linked to a carrier (i.e., a substance that stabilizes or otherwise improves the immunogenicity of an associated molecule), and optionally administered with an adjuvant (see, e.g., Ausubel et al., supra). An exemplary carrier is keyhole limpet hemocyanin (KLH) and exemplary adjuvants, which will typically be selected in view of the host animal's species, include Freund's adjuvant (complete or incomplete), adjuvant mineral gels (e.g., aluminum hydroxide), surface active substances such as lysolecithin, pluronic polyols, polyanions, peptides, oil emulsions, dinitrophenol, BCG (bacille Calmette-Guerin), and *Corynebacterium parvum*. KLH is also sometimes referred to as an adjuvant. The antibodies generated in the host can be purified by, for example, affinity chromatography methods in which the polypeptide antigen or a fragment thereof, is immobilized on a resin.

Epitopes encompassed by an antigenic peptide will typically be located on the surface of the protein (e.g., in hydrophilic regions), or in regions that are highly antigenic (such regions can be selected, initially, by virtue of containing many charged residues). An Emini surface probability analysis of human protein sequences can be used to indicate the regions that have a particularly high probability of being localized to the surface of the protein.

The antibody can be a fully human antibody (e.g., an antibody made in a mouse or other mammal that has been genetically engineered to produce an antibody from a human immunoglobulin sequence, such as that of a human immunoglobulin gene (the kappa, lambda, alpha (IgA1 and IgA2), gamma (IgG1, IgG2, IgG3, IgG4), delta, epsilon and mu constant region genes or the myriad immunoglobulin variable region genes). Alternatively, the antibody can be a non-human antibody (e.g., a rodent (e.g., a mouse or rat), goat, rabbit, or non-human primate (e.g., monkey) antibody).

Human monoclonal antibodies can be generated in transgenic mice carrying the human immunoglobulin genes rather than those of the mouse. Splenocytes obtained from these mice (after immunization with an antigen of interest) can be used to produce hybridomas that secrete human mAbs with specific affinities for epitopes from a human protein (see, e.g., WO 91/00906, WO 91/10741; WO 92/03918; WO 92/03917; Lonberg et al., 1994, Nature 368:856-859; Green et al., 1994, Nature Genet. 7:13-21; Morrison et al., 1994, Proc. Natl. Acad. Sci. USA, 81:6851-6855; Bruggeman et al., 1993, Immunol., 7:33-40; Tuaillon et al., 1993, Proc. Natl. Acad. Sci. USA, 90:3720-3724; and Bruggeman et al., 1991, Eur. J. Immunol., 21:1323-1326).

The anti-TLR2 antibody (e.g., 11G7) can also be one in which the variable region, or a portion thereof (e.g., a CDR), is generated in a non-human organism (e.g., a rat or mouse). Thus, the invention encompasses chimeric, CDR-grafted, and humanized antibodies and antibodies that are generated in a non-human organism and then modified (in, e.g., the variable framework or constant region) to decrease antigenicity in a human. Chimeric antibodies (i.e., antibodies in which different portions are derived from different animal species (e.g., the variable region of a murine mAb and the constant region of a human immunoglobulin) can be produced by recombinant techniques known in the art. For example, a gene encoding the Fc constant region of a murine (or other species) monoclonal antibody molecule can be digested with restriction enzymes to remove the region encoding the murine Fc, and the equivalent portion of a gene encoding a human Fc constant region can be substituted therefore (see, e.g., European Patent Application Nos. 125, 023; 184,187; 171,496; and 173,494; see also WO 86/01533; U.S. Pat. No. 4,816,567; Better et al., 1988, Science, 240: 1041-1043; Liu et al., 1987, Proc. Natl. Acad. Sci. USA, 84:3439-3443; Liu et al., 1987, J. Immunol., 139:3521-3526; Sun et al., 1987, Proc. Natl. Acad. Sci. USA, 84:214-218; Nishimura et al., 1987, Cancer Res., 47:999-1005; Wood et al., 1985, Nature, 314:446-449; Shaw et al., 1988, J. Natl. Cancer Inst., 80:1553-1559; Morrison et al., 1984, Proc. Natl. Acad. Sci. USA, 81:6851; Neuberger et al., 1984, Nature, 312:604; and Takeda et al., 1984, Nature, 314:452). In some embodiments, the antibody is produced by a hybridoma cell line deposited with the American Type Culture Collection under deposit no. PAT-5014.

In a humanized or CDR-grafted antibody, at least one or two, but generally all three of the recipient CDRs (of heavy and or light immunoglobulin chains) will be replaced with a donor CDR (see, e.g., U.S. Pat. No. 5,225,539; Jones et al., 1986, Nature, 321:552-525; Verhoeyan et al., 1988, Science, 239:1534; and Beidler et al., J. Immunol., 141:4053-4060, 1988). One need replace only the number of CDRs required for binding of the humanized antibody to TLR2 or a fragment of the extracellular domain thereof. The donor can be a rodent antibody, and the recipient can be a human framework or a human consensus framework. Typically, the immunoglobulin providing the CDRs is called the "donor" (and is often that of a rodent) and the immunoglobulin providing the framework is called the "acceptor." The acceptor framework can be a naturally occurring (e.g., a human) framework, a consensus framework or sequence, or a sequence that is at least 85% (e.g., 90%, 95%, 99%) identical thereto. A "consensus sequence" is one formed from the most frequently occurring amino acids (or nucleotides) in a family of related sequences (see, e.g., Winnaker, *From Genes to Clones*, Verlagsgesellschaft, Weinheim, Germany, 1987). Each position in the consensus sequence is occupied by the amino acid residue that occurs most frequently at that position in the family (where two occur equally frequently, either can be included). A "consensus framework" refers to the framework region in the consensus immunoglobulin sequence. Humanized TLR2 antibodies can be made in which specific amino acid residues have been substituted, deleted or added (in, e.g., in the framework region to improve antigen binding). For example, a humanized antibody will have framework residues identical to those of the donor or to amino acid a receptor other than those of the recipient framework residue. To generate such antibodies, a selected, small number of acceptor framework residues of the humanized immunoglobulin chain are replaced by the corresponding donor amino acids. The substitutions can occur adjacent to the CDR or in regions that interact with a CDR (U.S. Pat. No. 5,585,089, see especially columns 12-16). Other techniques for humanizing antibodies are described in EP 519596 A1.

A TLR2 antibody (e.g., 11G7) can be humanized as described above or using other methods known in the art. For example, humanized antibodies can be generated by replacing sequences of the Fv variable region that are not directly involved in antigen binding with equivalent sequences from human Fv variable regions. General methods for generating humanized antibodies are provided by Morrison (1985, Science, 229:1202-1207), Oi et al. (1986, BioTechniques, 4:214), and Queen et al. (U.S. Pat. Nos. 5,585,089; 5,693,761, and 5,693,762). The nucleic acid sequences required by these methods can be obtained from a hybridoma producing an antibody against a TLR2 or fragments thereof having the desired properties such as the ability to block induction of cytokines by araLAM, but not zymosan. The recombinant DNA encoding the humanized antibody, or fragment thereof, can then be cloned into an appropriate expression vector.

In certain embodiments, the antibody has an effector function and can fix complement, while in others it can neither recruit effector cells nor fix complement. The antibody can also have little or no ability to bind an Fc receptor. For example, it can be an isotype or subtype, or a fragment or other mutant that cannot bind to an Fc receptor (e.g., the antibody can have a mutant (e.g., a deleted) Fc receptor binding region). Antibodies lacking the Fc region typically cannot fix complement, and thus are less likely to cause the death of the cells they bind to.

In other embodiments, the antibody can be coupled to a heterologous substance, such as a therapeutic agent (e.g., an antibiotic), or a detectable label. A detectable label can include an enzyme (e.g., horseradish peroxidase, alkaline phosphatase, β-galactosidase, or acetylcholinesterase), a prosthetic group (e.g., streptavidin/biotin and avidin/biotin), or a fluorescent, luminescent, bioluminescent, or radioactive material (e.g., umbelliferone, fluorescein, fluorescein isothiocyanate, rhodamine, dichlorotriazinylamine fluorescein, dansyl chloride or phycoerythrin (which are fluorescent), luminol (which is luminescent), luciferase, luciferin, and aequorin (which are bioluminescent), and $^{99m}$Tc, $^{188}$Re, $^{111}$In, $^{125}$I, $^{131}$I, $^{35}$S or $^{3}$H (which are radioactive)).

The antibodies described herein (e.g., monoclonal antibodies) can also be used to isolate TLR2 proteins or fragments thereof such as the fragment associated with cytokine induction by araLAM (by, for example, affinity chromatography or immunoprecipitation) or to detect them in, for example, a cell lysate or supernatant (by Western blotting, enzyme-linked immunosorbant assays (ELISAs), radioimmune assays, and the like) or a histological section. These methods permit the determination of the abundance and pattern of expression of a particular protein. This information can be useful in making a diagnosis or in evaluating the efficacy of a clinical test or treatment.

The invention also includes the nucleic acids that encode the antibodies described above and vectors and cells (e.g., mammalian cells such as CHO cells or lymphatic cells) that contain them (e.g., cells transformed with a nucleic acid that encodes an antibody that specifically binds to TLR2). Similarly, the invention includes cell lines (e.g., hybridomas) that make the antibodies of the invention and methods of making those cell lines.

Screening Assays

The invention provides methods (also referred to herein as "screening assays") for identifying modulators, i.e., candidate or test compounds or agents (e.g., peptides, peptidomimetics, small molecules or other drugs) that specifically bind to TLR1 or TLR2 and disrupt signaling through these two proteins, e.g., by inhibiting the formation of TLR1/TLR2 complexes (e.g., inhibiting binding of TLR2 and TLR1) or by inhibiting ligand binding to TLR1/TLR2 complexes (e.g., by competitively inhibiting binding). In general, such compounds specifically bind to TLR2 and, in addition to this property, also inhibit cytokine expression that is inducible with araLAM or Pam$_3$CSK$_4$ and do not inhibit cytokine expression that is induced by zymosan. Cytokines that can be assayed include IL-6 and derivatives thereof.

Candidate compounds are useful as part of a strategy to identify drugs for treating disorders involving cytokine induction via pathways involving TLR1/TLR2 interaction. A test compound that binds to TLR1 or TLR2 is considered a candidate compound.

Screening assays for identifying candidate or test compounds that bind to TLR1 or TLR2, or modulate the activity of TLR2 proteins or polypeptides or biologically active portions thereof, are also included in the invention. The test compounds can be obtained using any of the numerous approaches in combinatorial library methods known in the art, including, but not limited to, biological libraries; spatially addressable parallel solid phase or solution phase libraries; synthetic library methods requiring deconvolution; the "one-bead one-compound" library method; and synthetic library methods using affinity chromatography selection. The biological library approach can be used for, e.g., peptide libraries, while the other four approaches are applicable to peptide, non-peptide oligomer or small molecule libraries of compounds (Lam, 1997, Anticancer Drug Des., 12:145). Examples of methods for the synthesis of molecular libraries can be found in the art, for example in: DeWitt et al., 1993, Proc. Natl. Acad. Sci. U.S.A., 90:6909; Erb et al., 1994, Proc. Natl. Acad. Sci. USA, 91:11422; Zuckermann et al., 1994,. J. Med. Chem., 37:2678; Cho et al., 1993, Science, 261:1303; Carrell et al., 1994, Angew. Chem. Int. Ed. Engl., 33:2059; Carell et al., 1994, Angew. Chem. Int. Ed. Engl., 33:2061; and Gallop et al., 1994, J. Med. Chem., 37:1233. In some embodiments, the test compounds are dominant negative variants of TLR or TLR2, e.g., as described herein (see Example 5, below).

Libraries of compounds can be presented in solution (e.g., Houghten, 1992, Bio/Techniques, 13:412-421), or on beads (Lam, 1991, Nature, 354:82-84), chips (Fodor, 1993, Nature, 364:555-556), bacteria (U.S. Pat. No. 5,223,409), spores (U.S. Pat. Nos. 5,571,698, 5,403,484, and 5,223,409), plasmids (Cull et al., 1992, Proc. Natl. Acad. Sci. USA, 89:1865-1869) or on phage (Scott and Smith, 1990, Science, 249: 386-390; Devlin, 1990, Science, 249:404-406; Cwirla et al., 1990, Proc. Natl. Acad. Sci. USA, 87:6378-6382; and Felici, 1991, J. Mol. Biol., 222:301-310).

The ability of a test compound to modulate the activity of a TLR2 or a biologically active portion thereof can be determined, e.g., by monitoring the ability of the TLR2 protein to bind to or interact with a TLR1 and/or TLR6 molecule in the presence of the test compound. The ability of the test compound to modulate the activity of TLR2 or a biologically active portion thereof can also be determined by monitoring the ability of the TLR2 protein to bind to CDC14. Such assays may be in the presence of TLR1. The binding assays can be cell-based or cell-free (described infra).

The ability of a TLR2 protein to bind to or interact with TLR1, TLR6 or CD14 can be determined by one of the methods described herein or known in the art for determining direct binding. In one embodiment, the ability of the TLR2 protein to bind to or interact with TLR1, TLR6, or CD14 can be determined by monitoring the induction of a cytokine, e.g., IL-6. Detection of the cytokine can include detection of the expression of a recombinant cytokine that also encodes a detectable marker such as a FLAG sequence or a luciferase. This assay can be in addition to an assay of direct binding. In general, such assays are used to determine the ability of a test compound to affect the binding of TLR1 to TLR2 or TLR2 to TLR6.

In another embodiment of the invention, the ability of a test compound to modulate activity associated with signaling through TLR1/TLR2 or TLR2/TLR6, or the binding of TLR1 to TLR2 or TLR2 to TLR6, can be determined by assaying the ability of the test compound to modulate TLR1/TLR2-dependent pathways or processes. Such pathways or processes include the capping of TLR1/TLR2 and induction of NF-κB, as well as the induction of cytokines (e.g., IL-6), as discussed herein and shown in the Examples. The assays include known cell-based or cell-free assays appropriate for the specific pathway or process of interest.

A cell-free assay can comprise contacting a TLR2 or TLR1 protein or biologically active portion thereof with a test compound and determining the ability of the test compound to bind to the TLR1 or TLR2 protein or biologically active portion thereof. Binding of the test compound to the TLR1 or TLR2 protein can be determined either directly or indirectly as described above. In one embodiment, a competitive binding assay includes contacting the TLR1 or TLR2 protein or biologically active portion thereof (e.g., the port of TLR1 that interacts with TLR2 and vice versa) with a TLR2 (in the case of a TLR1) or a TLR1 (in the case of a TLR2) to form an assay mixture, contacting the assay mixture with a test compound, and determining the ability of the test compound to interact with the TLR2 or TLR1 protein, wherein determining the ability of the test compound to interact with the TLR2 or TLR1 protein includes determining the ability of the test compound to preferentially bind to TLR1 or TLR2 or a biologically active portion thereof as compared to the known binding compound (e.g., TLR1 in the case of TLR2 and vice versa). Similar assays can be done to identify test compounds that do affect the TLR1-TLR2 interaction, but not the TLR2-TLR6 interaction.

In another embodiment, an assay is a cell-free assay that includes contacting a TLR2 protein or biologically active portion thereof with a test compound and determining the ability of the test compound to modulate (inhibit) the activity of the TLR2 protein or biologically active portion thereof. The ability of the test compound to modulate the activity of TLR2 can be determined, for example, by monitoring the ability of the TLR2 protein to bind to TLR1 or TLR6 by one of the methods described above for determining direct binding or TLR2-mediated signaling.

In yet another embodiment, the cell-free assay includes contacting the TLR2 protein or biologically active portion thereof with TLR1 or TLR6 to form an assay mixture, contacting the assay mixture with a test compound, and determining the ability of the test compound to interact with a TLR2 protein, wherein determining the ability of the test compound to interact with a TLR2 protein involves determining the ability of the TLR2 protein to preferentially bind to TLR1 or TLR6. The cell-free assays of the present invention are amenable to use of both soluble forms or membrane-associated forms of TLR2. In the case of cell-free assays comprising membrane-associated form of TLR2, it may be desirable to utilize a solubilizing agent such that the membrane-associated form of TLR2 is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, TRITON™ X-100, TRITON™ X-114, THESIT™, isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In some embodiments of the assay methods described herein, it may be desirable to immobilize TLR2, TLR1, or TLR6 to facilitate separation of complexed from uncomplexed forms of one or both of the proteins, as well as to accommodate automation of the assay. Assays for evaluating the binding of a test compound to TLR2, or interaction of TLR2 with TLR1 or TLR6 (e.g., binding or cytokine induction) in the presence or absence of a test compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/TLR2, TLR6, or /TLR1 fusion proteins or glutathione-S-transferase/target fusion proteins can be adsorbed onto glutathione Sepharose™ beads (Sigma Chemical; St. Louis, Mo.) or glutathione derivatized microtitre plates, which are then combined with the test compound or the test compound and either the non-adsorbed target protein or TLR2, TLR6, or TLR1 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of TLR2 binding or activity (e.g., induction of cytokine expression) determined using known techniques.

In an alternative embodiment, MYC or HA epitope tagged TLR2 fusion proteins or MYC or HA epitope tag target fusion proteins can be adsorbed onto anti-MYC or anti-HA antibody coated microbeads or onto anti-MYC or anti-HA antibody coated microtitre plates, which are then combined with the test compound or the test compound and non-adsorbed TLR1, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of TLR1/TLR2 or TLR2/TLR6 binding or activity determined using known techniques.

Other techniques for immobilizing proteins on matrices can also be used in the screening assays of the invention. For example, TLR2, TLR6, or TLR1 can be immobilized utilizing conjugation of biotin and streptavidin. Biotinylated TLR2, TLR6 or TLR1 can be prepared from biotin-NHS (N-hydroxy-succinimide) using techniques known in the art (e.g., biotinylation kit, Pierce Chemicals; Rockford, Ill.), and immobilized in the wells of streptavidin-coated 96 well plates (Pierce Chemical). Alternatively, antibodies reactive with TLR2, TLR6, or TLR1, but which do not interfere with binding of the TLR2 and TLR1 or TLR2 and TLR6 proteins, or activity of TLR2/TLR2 and/or TLR2/TLR6, can be derivatized to the wells of the plate, and unbound TLR2, TLR6 or TLR1 is trapped in the wells by antibody conjugation. Methods for detecting such complexes, in addition to those described above for the GST-immobilized complexes and epitope tag immobilized complexes, include immunodetection of complexes using antibodies reactive with the TLR2 or TLR1, as well as enzyme-linked assays that rely on detecting an enzymatic activity associated with the TLR.

In an embodiment of the invention, the ability of a test compound to modulate the binding or activity of TLR2 and TLR1 or TLR2 and TLR6, or a biologically active portion thereof can be determined by assaying the ability of the test compound to block the binding of TLR1 to TLR2, or TLR6 to TLR2, in a two-hybrid system assay. To screen for test compounds that block binding of TLR1 to TLR2, a yeast two-hybrid screening strain coexpressing the interacting bait and prey constructs, for example, a TLR1 bait construct and a TLR2 prey construct, is contacted with the test compound and the activity of the two-hybrid system reporter gene, for example, HIS3, lacZ, or URA3 is assayed. If the strain remains viable, but exhibits a significant decrease in reporter gene activity, this indicates that the test compound has inhibited the interaction between the bait and prey proteins. This assay can be automated for high throughput screening purposes, for example, for identifying candidate drugs. In another embodiment of the invention, TLR1 and TLR2 can be configured in the reverse two-hybrid system (Vidal et al., 1996, Proc. Natl. Acad. Sci. USA 93:10321-6 and Vidal et al., 1996, Proc. Natl. Acad. Sci. USA 93:10315-20) designed specifically for efficient drug screening. In the reverse two-hybrid system, inhibition of a TLR1/TLR2 physical interaction results in induction of a reporter gene in contrast to the conventional two-hybrid system in which inhibition of TRL1/TLR2 physical interaction leads to reporter gene repression.

In another embodiment, fluorescence transfer between two fluor-labeled proteins can be used to identify test compounds that inhibit binding of TLR1 to TLR2, but do not significantly inhibit binding of TLR2 to TLR6. A number of such methods are known in the art, e.g., FRET, and can be adapted for thigh-throughput screening of libraries of test compounds.

In general, the ability of a test compound to bind to TLR2; interfere with signaling through TLR1/TLR2, but not interfere with signaling through TLR2/TLR6; or otherwise affect the induction of cytokine expression is compared to a control in which the binding or induction of cytokine expression is determined in the absence of the test compound. In some cases, a predetermined reference value is used. Such reference values may be determined relative to controls, in which case a test sample that is different from the reference would indicate that the compound binds to the molecule of interest (e.g., TLR2) or affects expression (e.g., increases or decreases induction of cytokine expression). A reference value can also reflect the amount of binding or induction of cytokine expression observed with a standard (e.g., the affinity of 11G7 for TLR2, or induction of cytokine expression in the presence of 11G7). In this case, a test compound that is similar to (e.g., equal to or less than) the reference would indicate that compound is a candidate compound (e.g., binds to TLR2 to a degree equal to or greater than 11G7).

This invention further pertains to novel agents identified by the above-described screening assays and uses thereof for treatments as described herein.

Pharmaceutical Compositions

The agents described herein, e.g., antibodies or other compounds that specifically bind to TLR2 and inhibit signaling by TLR1/TLR2, but do not significantly inhibit signaling by TLR2/TLR6, can be incorporated into pharmaceutical compositions. Such compositions typically include the agent (e.g., antibody) and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, inhalation, transdermal (topical), transmucosal, or rectal; or oral. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL™, or corn starch; a lubricant such as magnesium stearate or STEROTES™; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa, butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models, e.g., of inflammation or disorders involving undesirable inflammation, to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography, generally of a labeled agent. Animal models useful in studies, e.g., preclinical protocols, are known in the art, for example, animal models for inflammatory disorders such as those described in Sonderstrup (2003, Springer Sem. Immunopathol., 25:35-45) and Nikula et al. (2000, Inhal. Toxicol., 12 Suppl. 4:123-53), and those known in the art, e.g., for fungal infection, sepsis, cytomegalovirus infection, tuberculosis, leprosy, viral hepatitis, and infection (e.g., by mycobacteria).

As defined herein, a therapeutically effective amount of protein or polypeptide such as an antibody (i.e., an effective dosage) ranges from about 0.001 to 30 mg/kg body weight, for example, about 0.01 to 25 mg/kg body weight, about 0.1 to 20 mg/kg body weight, or about 1 to 10 mg/kg, 2 to 9 mg/kg, 3 to 8 mg/kg, 4 to 7 mg/kg, or 5 to 6 mg/kg body weight The protein or polypeptide can be administered one or several times per day or per week for between about 1 to 10 weeks, for example, between 2 to 8 weeks, between about 3 to 7 weeks, or about 4, 5, or 6 weeks. In some instances the dosage may be reuired over several months or more. The skilled artisan will appreciate that certain factors may influence the dosage and timing required to effectively treat a subject, including, but not limited to the severity of the disease or disorder, previous treatments, the general health and/or age of the subject, and other diseases present. Moreover, treatment of a subject with a therapeutically effective amount of an agent such as a protein or polypeptide (including an antibody) can include a single treatment or, preferably, can include a series of treatments.

For antibodies, the dosage is generally 0.1 mg/kg of body weight (for example, 10 mg/kg to 20 mg/kg). Partially human antibodies and fully human antibodies generally have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. (1997, J. Acquired Immune Deficiency Syndromes and Human Retrovirology, 14:193).

The present invention encompasses agents or compounds that modulate expression or activity of cytokines by modulating signaling through TLR1/TLR2, but do not modulate signaling through TLR2/TLR6. An agent may, for example, be a small molecule. Such small molecules include, but are not limited to, peptides, peptidomimetics (e.g., peptoids), amino acids, amino acid analogs, small non-nucleic acid organic compounds or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (e.g., 11G7) or fragment thereof may be linked, e.g., covalently and/or with a linker to another therapeutic moiety such as a therapeutic agent or a radioactive metal ion, to form a conjugate. Therapeutic agents include, but are not limited to, antibiotics (e.g., dactinomycin (formerly actinomycin), bleomycin, mithramycin, and anthramycin (AMC)).

The conjugates described herein can be used for modifying a given biological response. For example, the moiety bound to the antibody may be a protein or polypeptide possessing a desired biological activity. Such proteins may include, for example, a toxin such as abrin, ricin A, Pseudomonas exotoxin, or diphtheria toxin; a protein such as tumor necrosis factor, α-interferon, β-interferon, nerve growth factor, platelet derived growth factor, tissue plasminogen activator; or, biological response modifiers.

Alternatively, an antibody can be conjugated to a second antibody to form an antibody heteroconjugate as described by Segal in U.S. Pat. No. 4,676,980.

The pharmaceutical compositions can be included in a container, pack, or dispenser together with instructions for administration.

Compounds as described herein may be used for the preparation of a medicament for use in any of the methods of treatment described herein.

Methods of Treatment

Also described herein are both prophylactic and therapeutic methods of treating a subject at risk of (or susceptible to) a disorder or having a disorder associated with undesirable TLR2 expression or activity.

Prophylactic Methods

The invention relates to methods for preventing in a subject a disease or condition associated with an undesirable amount of TLR2 expression or activity, by administering to the subject an agent that modulates signaling through TLR1/TLR2, but not signaling through TLR2/TLR6. An example of such an agent is 11G7. Subjects at risk for a disorder or undesirable symptoms that are caused or contributed to by TLR1/TLR2-mediated signaling can be identified by, for example, any of a combination of diagnostic or prognostic assays as described herein or are known in the art. In general, such disorders involve undesirable activation of the innate immune system, e.g., undesirable induction of cytokines such as IL-6. Administration of the agent as a prophylactic agent can occur prior to the manifestation of symptoms, such that the symptoms are prevented, delayed, or diminished compared to symptoms in the absence of the agent. In some embodiments, the agent decreases binding of TLR1 to TLR2, but not binding of TLR2 to TLR6. In some embodiments, the agent decreases ligand binding to TLR1/TLR2, but not to TLR2/TLR6. The appropriate agent can be identified based on screening assays described herein. In general, such agents specifically bind to TLR2 and inhibit signaling through TLR1/TLR2, but do not significantly inhibit signaling through TLR2/TLR6, e.g., specifically inhibit cytokine expression induced by certain compounds (e.g., araLAM) and do not significantly inhibit cytokine expression induced by other compounds (e.g., zymosan).

Therapeutic Methods

Another aspect of the invention pertains to methods of modulating TLR2 expression or activity for therapeutic purposes. The method can include contacting a cell with an agent that modulates one or more of the activities of TLR2 activity associated with the cell, e.g., specifically binds to TLR2 and inhibits signaling through TLR1/TLR2 and, in some embodiments, does not significantly inhibit signaling through TLR2/TLR6. The agent can be a compound that specifically binds to TLR2 and selectively inhibits induction by araLAM or $Pam_3CSK_4$ and does not significantly inhibit induction by zymosan. The agent can be an antibody (e.g., 11G7) or a protein, a naturally-occurring cognate ligand of a TLR2 or TLR1 protein, a peptide, a TLR2 or TLR1 peptidomimetic, a small non-nucleic acid organic molecule, or a small inorganic molecule. These modulatory methods can be performed in vitro (e.g., by culturing the cell with the agent) or, alternatively, in vivo (e.g., by administering the agent to a subject).

The present invention provides methods of treating an individual affected by a disease or disorder characterized by undesirable expression or activity of a TLR2 protein; for example, undesirable cytokine activity. In one embodiment, the method involves administering an agent (e.g., an agent identified by a screening assay described herein), or combination of agents that decreases signaling through TLR1/TLR2 without significantly decreasing signaling through TLR2/TLR6. Conditions that can be treated by agents include those in which a subject exhibits undesirable activation of the innate immune system (e.g., undesirable inflammation).

Other disorders that can be treated by the new methods and compositions include fungal infections, sepsis, cytomegalovirus infection, tuberculosis, leprosy, bone resorption (e.g., in periodontal disease), arthritis (e.g., associated with Lyme disease), and viral hepatitis. Compounds that interfere with signaling through TLR1/TLR2 (e.g., by binding to TLR2), but do not significantly inhibit signaling through TLR2/TLR6 are also useful for selectively controlling cytokine production during inflammatory reactions, e.g., those produced in response to infection by microbes such as mycobacteria.

Successful treatment of disorders related to undesirable activation of the innate immune system such as undesirable inflammation reactions can be brought about by techniques that serve to inhibit the binding of TLR1 to TLR2, or inhibit the binding of ligands to TLR1/TLR2 complexes. For example, compounds, e.g., an agent identified using an assay described herein, such as the antibody 11G7, that prove to exhibit negative modulatory activity, can be used to prevent and/or ameliorate symptoms of disorders caused by undesirable TLR1 or TLR2 activity. Such molecules can include, but are not limited to peptides, phosphopeptides, small organic or inorganic molecules, or antibodies (including, for example, polyclonal, monoclonal, humanized, anti-idiotypic, chimeric or single chain antibodies, and Fab, F(ab')$_2$ and Fab expression library fragments, scFV molecules, and epitope-binding fragments thereof). In particular, antibodies and derivatives thereof (e.g., antigen-binding fragments thereof) that specifically bind to TLR2 and can prevent araLAM-induced cytokine expression in vitro and do not inhibit zymosan-induced expression in vitro (e.g., 11G7) are useful for such treatments.

This invention is further illustrated by the following examples which should not be construed as limiting.

EXAMPLES

Materials and Methods

Expression Vectors

Human TLR2 and TLR4 cDNAs were obtained from Tularik (San Francisco, Calif.). The TLR cDNAs encoded Flag-epitope tagged proteins and had been cloned into the pFlag-CMV-1 vector. Chimeric TLR2-TLR1 (termed TLR [2-1]) and TLR1-TLR2 (termed TLR [1-2]) constructs were generated by PCR as follows. An XhoI restriction site was ligated just upstream of Cys 577 of TLR1 and Cys 585 of TLR2 and used for the domain swapping. Intracellular and extracellular domains were PCR amplified using Pfu Turbo DNA polymerase (Stratagene) and cross-assembled into pBluescript II KS(+) (Stratagene).

The transmembrane and cytoplasmic regions of TLR1 and TLR2 were PCR amplified using the following primers: T2cyto-5, GCGCCTCGAGTGTCACAGGACAGCACTG-GTGTCTG (SEQ ID NO:1); TLR2-3, CGCGGGTAC-CCTAGGACTTTATCGCAGCTCTCAG (SEQ ID NO:2); T1cyto-5, GCGCCTCGAGTGCAACATAACTCTGCT-GATCGTCACC (SEQ ID NO:3); and TLR1-3, CGCGGG-TACCCTATTTCTTTGCTTGCTCTGTCAGC (SEQ ID NO:4). The PCR products were digested and cloned into the KpnI and XhoI sites of pBluescript II KS (+) (Stratagene).

A portion of the extracellular domain of TLR1 was PCR amplified using the following primers: TL1-Bam, CTTTCATTAGGATCCTCCAGCTGGTTTG (SEQ ID NO:5); T1ex-3, GCGCCTCGAGTTCAGACATGT-GAAAGTCCTTTAGTAGG (SEQ ID NO:6). The PCR product was digested with BamHI and XhoI and cloned into the BamHI and XhoI sites of the pBluescript vector already containing the cytoplasmic region of TLR2. This vector was then digested with BamHI and KpnI (KpnI site was blunted with Klenow enzyme) and the fragment containing the regions of TLR1 and TLR2 was inserted into the BamHI amd SmaI sites of pFlag-CMV-1 TLR1.II KS(+) (Stratagene).

A portion of the extracellular domain of TLR2 was PCR amplified using the following primers: TL2-RV, CTAACAT-TGATATCAGTAAGAATAGTTTTC (SEQ ID NO:7) and T2ex-3, GCGCCTCGAGCACCGAGAGGCGGACATC-CTGAACC (SEQ ID NO:8). The PCR product was digested with EcoRV and XhoI and cloned into the EcoRV and XhoI sites of the pBluescript vector already containing the cytoplasmic region of TLR1. This vector was then digested with EcoRV and KpnI. The KpnI site was blunted with Klenow enzyme. The EcoRV-KpnI fragment containing the cytoplasmic region of TLR1 was inserted into the EcoRV and SmaI sites of pFlag-CMV-1 TLR2.

Domain swapping was used to construct the vectors TLR [1-2 TIR] and TLR [2-1 TIR]. This was executed, in brief, using an NsiI restriction site that is conserved in TLR1 and TLR2. pCMV-Flag TLR1 was digested with NotI and partially digested with NsiI. A resulting 1917 bp fragment was cloned into the NotI and NsiI sites of the pBluescript containing the cytoplasmic region of TLR2. The resulting plasmid was then digested with NotI and KpnI and the fragment containing TLR [1-2 TIR] inserted into the NotI and KpnI sites of pFlag-CMV-1. A similar strategy was used to construct the TLR [2-1 TIR] vector.

Stimulants

Yeast zymosan was purchased from Sigma (St. Louis, Mo.). Mycobacterial araLAM was purified from rapidly growing avirulent mycobacteria using known methods (Dr. John Belisle; Colorado State University, Fort Collins, Colo.; under NIH contract, NIAID Contract NO1-AI-75320 entitled "Tuberculosis Research Materials and Vaccine Testing"). Pam$_3$CSK$_4$ was obtained from EMC Microcollections (Tubingen, Germany). Recombinant human IL-1R was purchased from R&D systems (Minneapolis, Minn.) and used as a positive control for NF-κB activation.

Example 1

Production of the 11G7 Monoclonal Antibody

An expression vector (pFLAGCMV1 vector) containing TLR2 cDNA (Genbank Accession No. NM_003264.2) was obtained from Tularik Inc. (South San Francisco, Calif.). This expression vector was transfected into HEK293 cells (ATCC accession no. CRL-1573). Transfected cells were used to immunize mice for monoclonal antibody production. Immunization involved intraperitoneal injection of transfected HEK293 cells with two boosts. Spleens from immunized mice were removed and isolated splenic cells were fused using known methods to make hybridoma cells. Transfected HEK293 cells expressing TLR2 protein were then used to screen hybridoma clones for antibodies that specifically bind to a TLR2. One such identified clone and antibody produced by that clone was termed "11G7."

Example 2

Anti-TLR1 and Anti-TLR2 Monoclonal Antibodies Block Cytokine Production by Human Peripheral Blood Mononuclear Cells (PBMCs) Stimulated with Ara-Lipoarabinomannan (AraLAM)

Genetic studies suggest that TLR2 is required for the recognition of a diverse group of microbial ligands, including araLAM and zymosan. The role of TLR1 and TLR2 in the response of normal human PBMCs to these ligands was analyzed in antibody blocking studies. In these studies, human PMBCs were stimulated in vitro, and the ability of anti-TLR1 or anti-TLR2 antibodies to inhibit stimulation was examined. Briefly, PBMCs were isolated from peripheral blood using Lymphocyte Separation Medium (Mediatech, Herndon, Va.). PBMCs were cultured in RPMI 1640 medium supplemented with 10% fetal calf serum (Atlanta Biologicals) in 24 well plates at $10^6$ cells/well. For blocking studies, prior to the additon of stimulants, PBMCs were preincubated for 30 minutes at 37° C. in 5% $CO_2$ with anti-TLR1 (clone GD2.F4, eBiosciences, San Diego, Calif.) or anti-TLR2 (clone 11G7) monoclonal antibodies, or isotype control antibody (eBiosciences, San Diego, Calif.) at 10 µg/ml per well. AraLAM was added to cultures at a concentration of 11 µg/ml and zymosan was added to cultures at a concentration of 10 µg/ml. The cultures were incubated for 18 hours at 37° C. in 5% $CO_2$. Supernatants were then prepared and levels of secreted IL-6 and/or IL-8 were determined by ELISA according to manufacturer's instructions (BD Pharmingen, OptEIA).

Figure 1A:
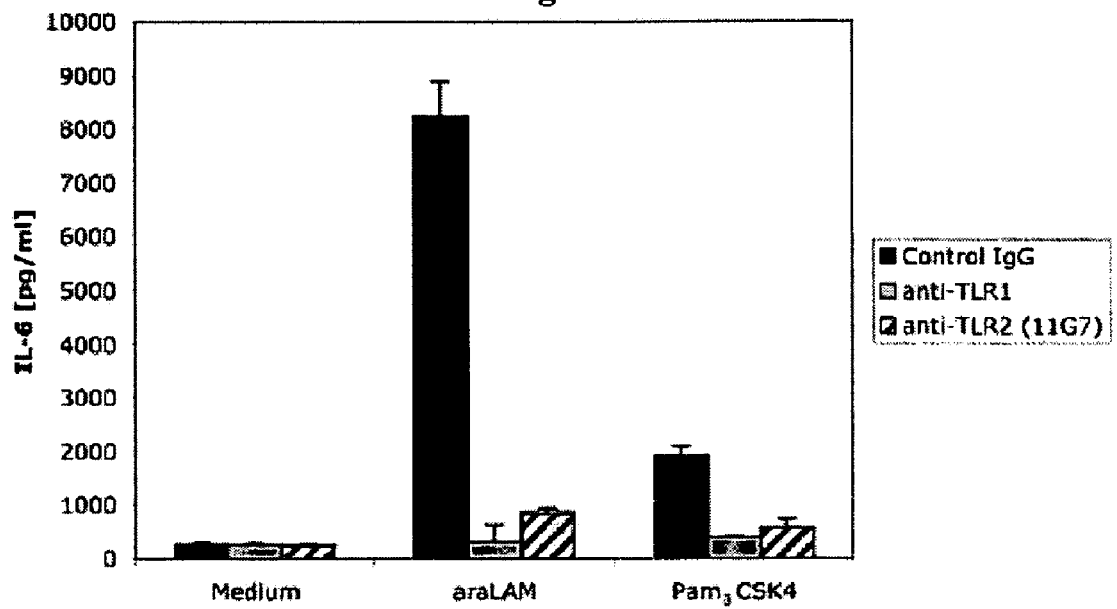
FIG. 1A is a bar graph depicting the results of enzyme linked immunosorbant assays (ELISAs) of the level of IL-6 expression in the presence or absence of TLR1 mAb (GD2.F4) or TLR2 mAb (11G7) in human PMBCs in the presence or absence of araLAM or $Pam_3CSK_4$.
Figure 1B:
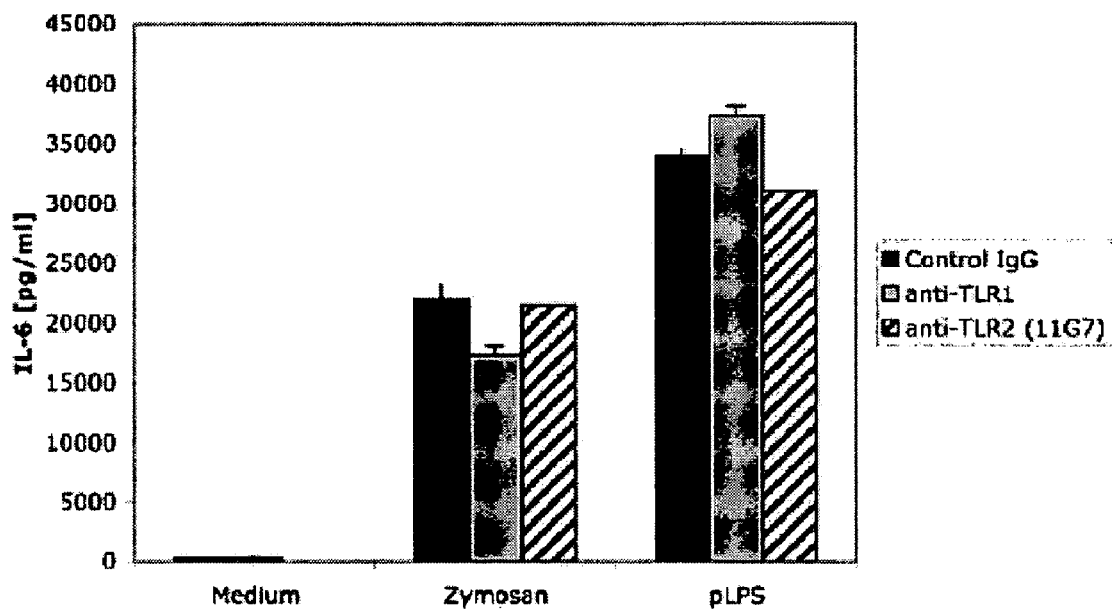
FIG. 1B is a bar graph depicting the results of ELISAs assaying the level of IL-6 expression in human PMBCs in the presence or absence of TLR1 mAb (GD2.F4) or TLR2 mAb (11G7), and in the presence or absence of zymosan or pLPS.

FIGS. 1A and 1B show representative results of at least three experiments each. Pre-treatment of PBMCs with either anti-TLR1 or anti-TLR2 (11G7) antibodies blocked IL-6 cytokine production in response to araLAM and $Pam_3CSK_4$ (FIG. 1A). In contrast, both antibodies failed to inhibit the IL-6 cytokine secretion after stimulation with zymosan (FIG. 1B). Moreover, as expected, addition of anti-TLR1 or -TLR2 antibodies to PBMCs did not exert any blocking effect to LPS stimulation (FIG. 1B). These results suggest that TLR1 and TLR2 both participate in the response to araLAM and $Pam_3CSK_4$, but that they act in a pathway that does not affect IL-6 secretion induced by zymosan.

These data demonstrate that 11G7 is effective for inhibition of cytokine secretion induced by araLAM.

Example 3

TLR1 Cooperates with TLR2 and CD14 on the Cell Surface to Initiate Signal Activation Both antibody blocking studies and TLR knockout animal studies suggest that TLR2 signaling involves cooperation with other TLR receptors, particularly TLR1 and TLR6. A functional signal transduction complex thus seems to require elements of both receptors. It was hypothesized that cross-linking TLR1 and TLR2 would mimic their engagement by a ligand and thus activate signal transduction and cytokine secretion. Accordingly, the ability of plate bound antibodies to TLRs to activate normal human cells was investigated.

In these experiments, PBMCs were incubated on sterile tissue culture plates coated with monoclonal antibodies to TLR1, TLR2 (2.1) and/or CD 14 alone or in combination. Briefly, anti-TLR1 (from clone GD2.F4, eBiosciences, San Diego, Calif.), anti-TLR2 (from clone TL2.1, Dr. Egil Lien, University of Massachusetts Medical School, available at eBiosciences, San Diego, Calif.), anti-CD14 (clone 26ic, ATCC accession no. HB-246) or isotype control OKT8 (ATCC no. CRL-8014) monoclonal antibodies in PBS were added to sterile high protein binding capacity 96-well plates (Costar) at concentrations varying from 0.2 to 0.8 µg/ml and incubated for 18 hours at 4° C. The plates were washed three times with PBS and blocked with 10% FCS (Atlanta Biologicals) in PBS for two hours. $7\times10^5$ PBMCs in RPMI with 10% FCS and 5 µg/ml polymyxin B were added to each well and incubated for 18 hours at 37° C. in 5% $CO_2$ in a humidified incubator. Low endotoxin monoclonal antibody preparations were used in all experiments. Polymyxin B (Sigma, catalog no. P4932) at 5 µg/ml concentration was added to the culture medium to neutralize potential endotoxin contamination. Supernatants were harvested and IL-8 levels were determined using ELISA according to manufacturer's instructions (Pharmingen).

The results (FIGS. 2A and 2B) show that a combination of anti-TLR1 and anti-TLR2-specific monoclonal antibodies activated IL-8 secretion from PBMCs in a dose-dependent manner. Individually, neither anti-TLR1, anti-TLR2, anti-CD14, nor isotype control antibodies alone were sufficient to elicit IL-8 secretion (FIG. 2A).

Experiments were conducted in which suboptimal concentrations of anti-TLR1 plus anti-TLR2 were immobilized on sterile high protein binding polystyrene 96-well plates at a concentration of 0.2 µg/ml together with increasing amounts of control (IgG) or anti-CD14 antibody. After blocking and washing, $7\times10^5$ human PBMCs were added to the antibody-coated wells in the presence of Polymyxin B (5 µg/ml). After 18 hours of incubation, supernatants were harvested and levels of IL-8 were measured by ELISA. The addition of anti-CD14 as a crosslinker enhanced IL-8 secretion in a dose-dependent manner suggesting a role for CD14 (or the membrane lipid microdomain in which CD14 resides) as an accessory molecule for TLR1-TLR2 activation (FIG. 2B).

Thus, when cells were stimulated with suboptimal levels of anti-TLR1 plus anti-TLR2 antibodies, co-crosslinking of CD14 enhanced cytokine production (FIG. 2B). These results indicate that CD14 significantly amplifies the cooperation of TLR1 and TLR2 receptors. Accordingly, compounds that inhibit CD14 expression or activity can be used to decrease activity such as cytokine expression that is induced by the interaction of TLR1 and TLR2.

Example 4

TLR1 Physically Associates with TLR2 Inside and on the Surface of Cells

The antibody blocking and cross-linking experiments supra suggested that TLR1 and TLR2 can associate in a functional signaling complex. The possibility that TLR1 and TLR2 associate in a physical interaction was investigated using confocal microscopy. In these experiments, HEK cells were stably transfected with TLR1 and TLR2 tagged at their C-terminus with yellow fluorescent (YFP) or cyan fluorescent proteins (CFP).

Briefly, stable cell lines of HEK293 cells stably expressing the both $TLR1^{YFP}$ and $TLR2^{CFP}$ (Latz et al., 2002, J. Biol. Chem. 6;277:47834-47843. Epub) were grown on glass-bottom tissue culture dishes and living cells were analyzed as described in above. Confocal microscopy was performed with living cells that were seeded on 35 mm glass bottom tissue culture dishes (MatTek Corp., Ashland, Mass.) 24-48 hours prior to examination. Images were taken with a Leica TCS SP2 AOBS confocal microscope equipped with an acousto-optical beamsplitter. The cells were kept at 37° C. during imaging using a warm stage apparatus. CFP-tagged proteins were visualized using the 458 rim argon laser line; for YFP the 514 rim line of a 100-mW argon laser was used. Alexa-647 was excited with a 2.5 mW helium/neon laser emitting at 633 nm. Cells expressing CFP and YFP proteins were sequentially scanned using only one laser line active per scan. This method of epitope tagging had no discernable effect on TLR function.

Cells transfected with $TLR2^{YFP}$ or $TLR4^{YFP}$ fusion proteins alone displayed a predominant membrane localization of TLR2. In contrast, $TLR1^{YFP}$ expressing cells displayed a diffuse pattern of cytoplasmic TLR1 distribution. Co-transfection of cells with $TLR1^{YFP}$ and $TLR2^{CFP}$ fusion proteins resulted in aggregation of TLR1 and TLR2 both on the surface and inside the cells. Antibody-induced aggregation of TLR2 on the surface of the cells led to coaggregation of TLR1, whereas antibody-induced surface aggregation of MHC I did not coaggregate TLR1 or TLR2. As a further control, TLR2 was surface aggregated in $TLR4^{YFP}$-expressing cells. Capping of TLR2 did not lead to coaggregation of TLR4, indicating the specificity of the observed coaggregation of TLR2 and TLR1. These results suggest that TLR1 and TLR2 are pre-assembled into heteromultimeric complexes on the cell surface.

Surface co-localization of TLR1 and TLR2 complexes was demonstrated with anti-TLR2, but not control anti-MHC Class I. In these experiments, TLR1-TLR2 co-transfected cells were incubated at 4° C. with anti-TLR2 or control anti-MHC Class I.

Surface-patching of TLR2 or MHC Class I was induced using Alexa647-labeled goat anti-mouse antisera ($2°^{AbAlexa647}$) followed by a ten minute incubation at 37° C. to cap the cell surface TLR2 or MHC I molecules. In these experiments, cells were grown on glass-bottom 35 mm tissue-culture dishes and washed twice with ice-cold Hank's Balanced Salt Solution (HBSS) containing 1% FBS. The cells were then incubated on ice for 30 minutes with primary antibodies; 5 μg/ml anti-TLR2 (clone TLR 2.1) and anti-human HLA I antibody (clone W6/32HL, Research Diagnostics Inc, catalog no. RDI-CBL139-1XP) in HBSS containing 1% FBS. After two washes with cold HBSS, the cells were counterstained with Alexa647-conjugated goat anti-mouse secondary antibody (Molecular Probes). The cells were then incubated in prewarmed complete growth medium for ten minutes at 37° C. and immediately analyzed by confocal microscopy.

Anti-TLR2 capping induced co-patching of TLR1 with TLR2 on the cell surface. MHC I cross-linking did not co-patch either $TLR2^{CFP}$ or $TLR1^{YFP}$ in the cells. These results demonstrate that the TLR1 specifically redistributes on the cell surface with TLR2 and suggest that TLR1 and TLR2 are pre-assembled into heterocomplexic complexes on the cell surface.

In summary, these data demonstrate that overexpression of TLR1 in HEK cells produced a diffuse pattern of distribution with TLR1 mainly localized inside the cells with a minimal cell membrane involvement. Expression of TLR2 resulted in a more prominent cell membrane localization. Overexpressing TLR1 in a TLR2 positive cell line produced aggregation of TLR1 and TLR2 receptors inside the cells as well as in the cell membrane. These results provide evidence of a physical interaction between TLR1 and TLR2.

Example 5

Dominant Negative TLR1 and TLR2 Inhibit the Response to araLAM and Zymosan—Loss of Function Studies HEK293 cells constitutively express a cytoplasmic pool of TLR1 that can be detected by fluorescent staining analysis of permeablized cells and TLR1 mRNA-specific RT-PCR. Transfection of HEK293 cells with wild type TLR2 is sufficient to confer responsiveness to both araLAM and zymosan (Kurt-Jones et al., 2002, Blood, 100:1860-1868). To investigate the role of TLR2 and TLR1 in response to araLAM and zymosan, various mutants of TLR2 and TLR1 proteins were generated. One mutant was based on a dominant negative mutation of the TIR domain of TLR4 found in the C3H/HeJ mice (Poltorak et al., 1998, Science, 282:2085-2088; Hoshino et al., 1999, J. Immunol., 162:3749-3752). In this mutant the corresponding homologous conserved proline within the TIR domain of TLR2 protein was mutated to histidine—TLR2 P681H.

A second TLR2 mutant was generated in which a stop codon was introduced at amino acid 643 resulting in the deletion of the conserved intracellular TIR domain—TLR2ΔTIR. Co-transfection experiments were performed to express increasing amounts of TLR2 mutant proteins with a constant amount of TLR2 wild type protein and the response of transfected cells to araLAM and zymosan was determined. Briefly, HEK293 cells (ATCC no. CRL-1573, Rockville, Md.) stably expressing human CD14 (HEK293-CD14) were cloned as previously described (Kurt-Jones et al., 2002, supra).

Transfections of HEK293-CD14 cells were performed using GeneJuice™ Transfection Reagent (Novagen, Madison, Wis.) according to manufacturer's instructions. The cells were plated into 96 well plates at $2.5 \times 10^4$/well and transfected 24 hours later with a total of 0.3 μg DNA per well. The transfected DNA included 80 ng of NF-κB-driven firefly luciferase plasmid (pGL-3-Basic Vector, Promega, catalog no. E1751) and 20 ng of HSV-TK promoter-driven renilla luciferase plasmid (phRL-TK Vector, Promega, catalog no. E6241), along with wild type or chimeric TLR constructs cloned into in pFlag-CMV-1 vector (Sigma, catalog no. E7273). TLR plasmids were transfected at concentrations ranging from 5 ng to 200 ng/well. Empty pFlag-CMV-1 vector was used to bring up the total amount of transfected DNA to 0.3 μg per well.

The transfected cells were incubated overnight at 37° C. in 5% $CO_2$ in a humidified incubator and then stimulated for six hours with zymosan (10 pg/ml), araLAM (1 μg/ml), $Pam_3CSK_4$ (100 ng/ml), or IL-1β (100 ng/ml). Cells were lysed using 50 μl of Passive Lysis Buffer (Promega, catalog no. E1941). Firefly luciferase activity in the lysate was measured using Dual-Glo™ Luciferase Assay System (Promega, catalog no. E2940) according to the manufacturer's instructions. Luciferase activity was calculated in relative light units (RLU) as a ratio of NF-κB-dependent firefly luciferase activity to NF-KB-independent renilla luciferase activity. The results are shown in FIGS. 3A and 3B as the mean±SD of triplicate wells and are representative of three independent experiments.

Figure 3A:
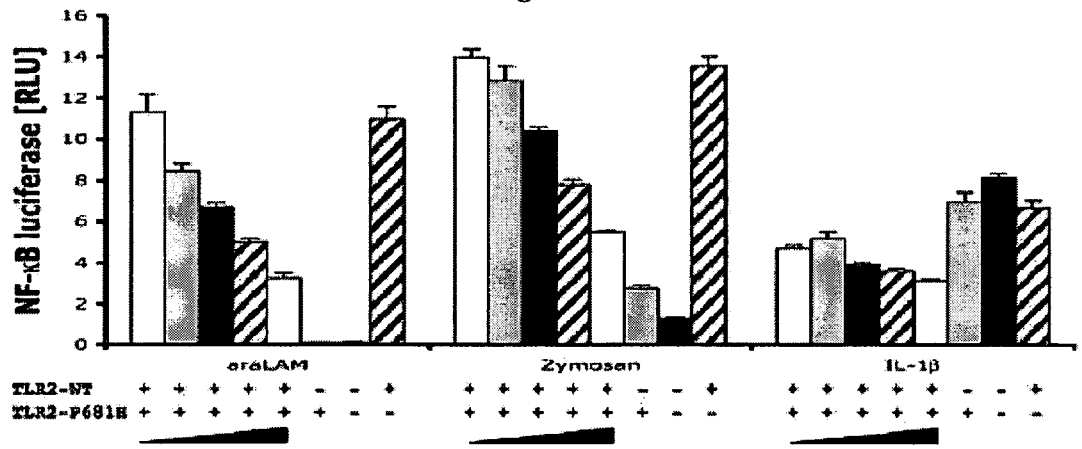
FIG. 3A is a set of bar graphs depicting the results of experiments in which HEK293-CD14 cells were incubated in the presence of araLAM or zymosan and NF-κB-luciferase expression assayed. TLR2-WT indicates that the cells were transfected with a wild type TLR2 expression construct and TLR2-P681H indicates that the cells were transfected with a single point mutated TLR2 construct. IL-1β was used as a positive control.
Figure 3B:
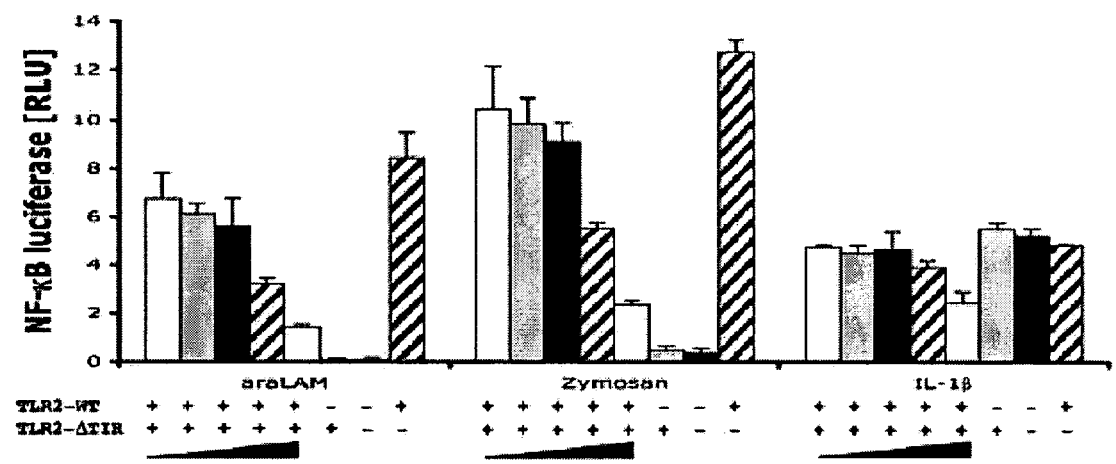
FIG. 3B is a set of bar graphs depicting the results of experiments in which the response of HEK293-CD14 cells to araLAM and zymosan in the presence of a TLR2 mutant missing the TIR domain; TLR2-ΔTIR. IL-1β was used as a positive control.

Transient transfection of HEK293-CD14 cells with increasing amounts of TLR2 mutants resulted in dose dependent impairment of NF-κB activation in response to both araLAM and zymosan (FIGS. 3A and 3B).

To analyze the role of TLR1, a cytoplasmic deletion mutant (TLR1Δcyt) was tested (Wyllie et al., 2000, J.

Figure 3C:
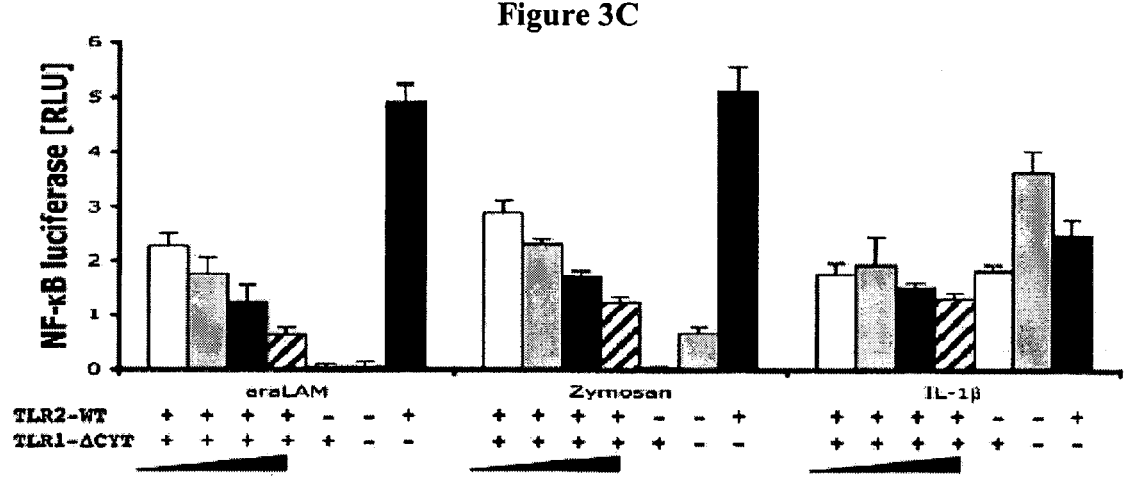
FIG. 3C is a set of bar graphs depicting the results of experiments in which the response of HEK293-CD14 cells to araLAM and zymosan was examined during expression of a cytoplasmic deletion mutant of TLR1-TLR1-Δcyt.

Immunol. 165:7125-7132). In this construct the intracellular protein sequence of TLR1 that is immediately after the transmembrane region is deleted, thus the TLR1 protein lacked the entire cytoplasmic domain including the TIR domain. This TLR1Δcyt truncation construct, when transfected together with TLR2 wild type protein into HeLa cells, has been shown to abrogate the response to *S. Minnesota* LPS preparation (Wyllie et al, 2000, supra). Transfection of HEK293-CD14 cells with increasing amounts of TLR1Δcyt truncation construct resulted in a dose-dependent decrease in NF-κB activation in response to both araLAM and zymosan (FIG. 3C). Thus, dominant negative forms of both TLR1 and TLR2 inhibit the NF-κB response to araLAM and zymosan. Such mutant proteins and fragments thereof are useful for disrupting TLR1/TLR2 interaction and inhibiting induction of cytokine activity.

Example 6

Figure 4A:
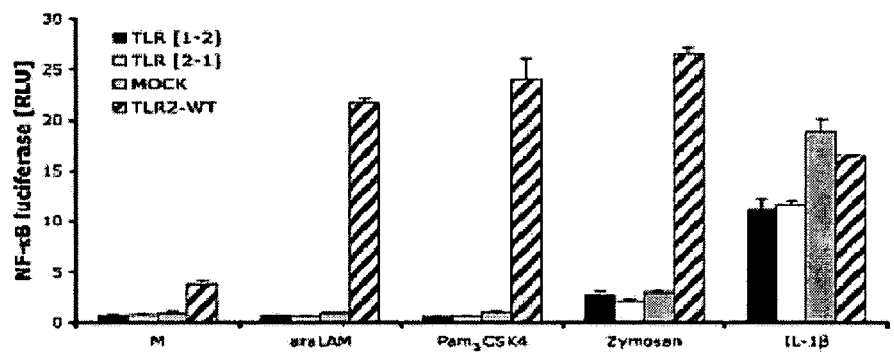
FIG. 4A is a bar graph illustrating the results of experiments in which HEK293-CD14 cells were transfected with either TLR [1-2] or TLR [2-1] DNA encoding chimeric protein, or wild type TLR2 DNA. IL-1β was used as a positive control.
Figure 4B:
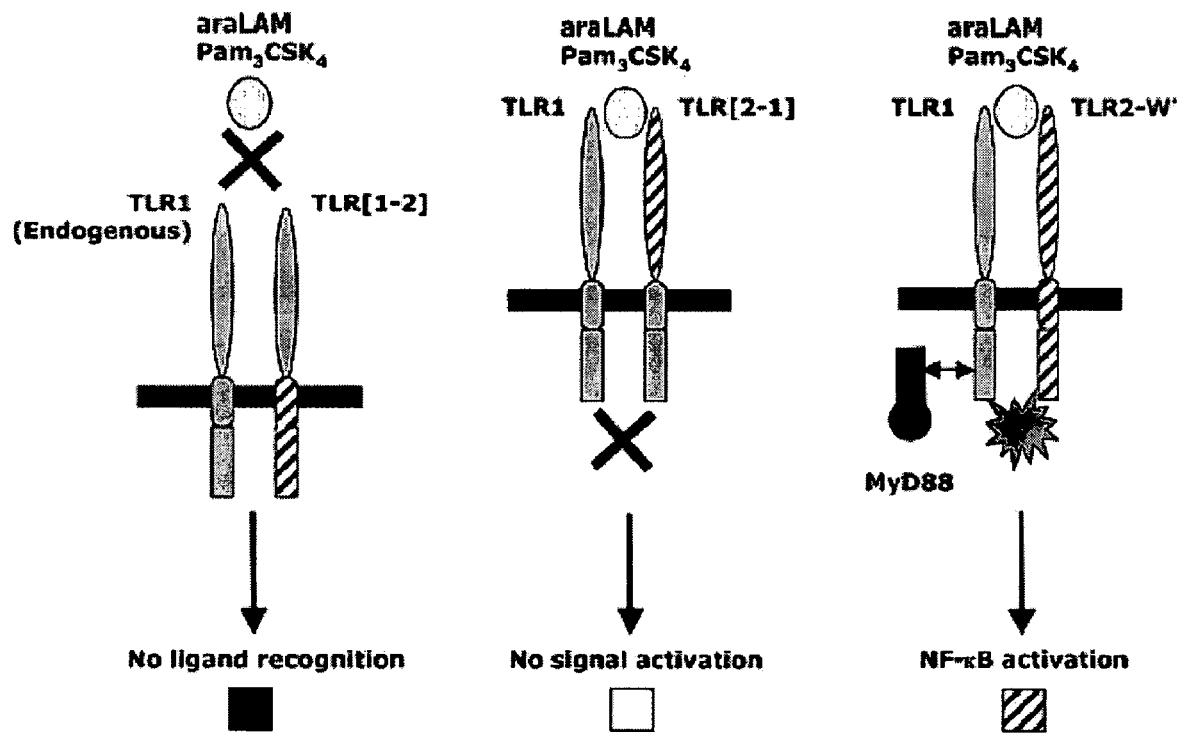
FIG. 4B is a schematic model of separate TLR1 and TLR2 chimeric protein transfection.

Neither the Extracellular Domain nor the Intracellular Domain of TLR2 Alone is Sufficient to Activate a NF-κB Dependent Response to araLAM, $Pam_3CSK_4$ or Zymosan To further understand the role of the TLR1 and TLR2 in ligand recognition, various types of TLR chimeric (fusion) proteins were generated by domain swapping of the extracellular and intracellular domains of TLR1, TLR2, and TLR4. Chimeric TLR proteins were transfected into HEK293-CD14 cells and the response of the cells to TLR ligands was determined. Cells transfected with a TLR [2-1] chimeric protein (consisting of the extracellular domain of the TLR2 fused to the intracellular domain of TLR1) did not respond to stimulation with araLAM, $Pam_3CSK_4$, and zymosan. Similarly, the reciprocal construct TLR [1-2] (with the extracellular domain of TLR1 fused to the intracellular domain of TLR2) did not elicit a response to any of these stimulants (FIG. 4A). FIG. 4B is a diagram illustrating a mechanism for TLR1/TLR2 interaction. With TLR1 endogenously expressed, transfection only of the intracellular portion of TLR2 (TLR [1-2]) does not confer responsiveness as a result of missing TLR2 extracellular domain causing ligand recognition failure. Transfection with only the extracellular portion of TLR2 (TLR [2-1]) is not sufficient to confer responsiveness since the TLR1 intracellular domain lacks the TLR2 intracellular domain for effective initiation of signaling pathways. With TLR1 endogenously present, transfection of TLR2-WT protein confers responsiveness by providing both extra- and intracellular domains needed for ligand recognition and signal activation respectively.

These results suggested that neither the extracellular domain of TLR2 nor the intracellular domain of TLR2 alone was sufficient to confer signaling in response to tested ligands. Similar results were obtained using TLR [1-4], TLR [2-3], TLR [4-1], and TLR [2-5] chimeric fusion proteins including their combinations. (Table 1).

TABLE 1

| Co-transfection of various TLR fusion proteins into HEK293-CD14 cells | | | |
|---|---|---|---|
| Transfected vectors | araLAM | Zymosan | IL-1β |
| TLR [1-2] | − | − | + |
| TLR [2-1] | − | − | + |
| TLR [2-1 TIR] | − | − | + |
| TLR [1-4] | − | − | + |
| TLR [4-1] | − | − | + |

TABLE 1-continued

| Co-transfection of various TLR fusion proteins into HEK293-CD14 cells | | | |
|---|---|---|---|
| Transfected vectors | araLAM | Zymosan | IL-1β |
| TLR [2-3] | − | − | + |
| TLR [2-4] | − | − | + |
| TLR [2-5] | − | − | + |
| TLR [1-2] + TLR [2-1] | + | − | + |
| TLR [1-2] + TLR [2-1 TIR] | + | − | + |
| TLR [1-2] + TLR [2-3] | − | − | + |
| TLR [1-4] + TLR [2-4] | − | − | + |
| TLR [1-4] + TLR [2-5] | − | − | + |

These experiments with chimeric proteins indicate that neither expression of TLR1 nor expression of TLR2 on the surface by itself, was sufficient for cytokine induction by araLAM. This suggests that araLAM must bind to the N terminal portions of both TLR 1 and TLR2 achieve cytokine induction by araLAM. Each TLR may contribute to a combined ligand binding site for araLAM. The use of C terminal chimeric proteins revealed that the C-termini of both TLR1 and TLR2 are necessary for ligand mediated induction of cytokines. Either TLR1 is associated with different signaling or adaptor proteins than TLR2 or both proteins interact with one another and this interaction is required for the association of adaptor molecules.

These experiments underscore the fact that: 1) TLR 1-TLR2 interactions occur naturally without ligand binding, 2) certain ligands can bind to both TLR1 and TLR2 extracellularly, and 3) intracellular interaction between TLR1 and TLR2 is necessary for induction of cytokines suggesting that different adaptor or signaling proteins are associated with different TLRs.

Example 7

Both Extracellular and Intracellular Domains of TLR1 and TLR2 are Required for Signaling in Response to araLAM or Pam_CSK₄

Neither the TLR [1-2] nor the TLR [2-1] chimeric proteins alone were sufficient to confer responsiveness to TLR2 ligands. Therefore, the ability of combinations of these chimeric fusion proteins to signal was examined. HEK293-CD14 cells were co-transfected with TLR [1-2] and TLR [2-1] fusion proteins, and the response of cells to araLAM, $Pam_3CSK_4$, and zymosan was tested. This combination of chimeric receptors was sufficient to confer responsiveness to araLAM and $Pam_3CSK_4$. The combination of TLR [1-2] and TLR [2-1] did not confer responsiveness to zymosan (FIG. 5A). FIG. 5B is a schematic diagram illustrating a mechanism derived from these data. Co-transfection of both chimeric proteins confers responsiveness as a result of concomitant expression of both intracellular and extracellular domains of TLR1 and TLR2. With TLR1 endogenously present, transfection with TLR2-WT alone is sufficient to confer responsiveness.

These results suggest that both intracellular and extracellular domains of TLR1 and TLR2 are required for recognition of araLAM and $Pam_3CSK_4$. Thus, it appears that within the intracellular domains of both receptors, complexization of TIR domains may be essential for subsequent signal activation.

To analyze the role of intracellular domain in signaling, another TLR fusion protein was generated, TLR [2-1 TIR], in which the TIR domain of TLR2 was replaced with the TIR domain of TLR1. Transfection with the TLR [2-1 TIR] construct alone did not confer responsiveness to araLAM and zymosan (Table 1). HEK293-CD14 cells cotransfected with TLR [1-2] fusion protein and TLR [2-1 TIR] fusion protein were activated in response to araLAM and Pam$_3$CSK$_4$, but not to zymosan (FIG. 6A).

FIG. 6B is a diagram illustrating a mechanism revealed by these data. Co-transfection of TLR [1-2] chimeric protein containing the entire intracellular domain of TLR2 (including the TIR domain) with the TLR [2-1 TIR] chimeric protein containing the TIR domain of TLR1, confers responsiveness. The transfected cells express the extracellular domains of TLR1 and TLR2 (ligand recognition) as well as both the TIR domains of TLR1 and TLR2 (signal transduction). With TLR1 endogenously present, transfection with TLR2-WT alone is sufficient to confer responsiveness. These data suggest that the heterocomplexization of the TIR domains of TLR1 and TLR2 is essential for the signaling in response to some, but not all, TLR2 ligands, i.e., araLAM and Pam$_3$CSK$_4$, but not zymosan.

Thus, compounds that interfere with the binding of TLR1 and TLR2 ligands can be used to selectively interfere with signaling in response to araLAM and Pam$_3$CSK$_4$ and not, e.g., zymosan. Similarly, compounds that mimic or promote the heterocomplexization of TIR domains of TLR1 and TLR2 are useful for selectively inducing the signaling response to araLAM and Pam$_3$CSK$_4$.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. An isolated 11G7 antibody or antigen-binding fragment thereof that specifically binds to Toll-like receptor-2 (TLR2).

2. A hybridoma cell line that produces the antibody of claim 1.

3. The cell line of claim 2, wherein the cell line is a mouse hybridoma cell line.

4. The cell line of claim 2, wherein the cell line is mouse hybridoma cell line 11G7.

5. The cell line of claim 3, wherein the cell line is deposited with the American Type Culture Collection under deposit no. PAT-5014.

6. A method of inhibiting TLR2 activation in a cell, the method comprising contacting the cell with the antibody of claim 1.

7. A pharmaceutical composition comprising the antibody of claim 1.

8. A method of decreasing inflammation in a subject, the method comprising administering to the subject the pharmaceutical composition of claim 7.

9. The antibody or antigen-binding fragment thereof of claim 1, wherein the antibody or antigen-binding fragment specifically binds to the extracellular domain of Toll-like receptor-2 protein (TLR2).

10. An isolated antibody or antigen-binding fragment thereof comprising antigen-binding portions of monoclonal antibody 11G7 that specifically bind to Toll-like receptor-2 (TLR2), wherein the antibody or antigen-binding fragment thereof is selected from the group consisting of a chimeric antibody, a recombinant antibody, a humanized antibody, and a single-chain antibody.

11. The antibody or antigen-binding fragment thereof of claim 10, wherein the antigen-binding fragment thereof comprises a single chain antibody.

12. The antibody or antigen-binding fragment thereof of claim 10, wherein the antibody or antigen-binding fragment thereof is chimeric.

13. A hybridoma cell line that produces the chimeric antibody or antigen-binding fragment thereof of claim 12.

14. The antibody or antigen-binding fragment thereof of claim 10, wherein the antibody or antigen-binding fragment thereof is humanized.

15. A hybridoma cell line that produces the humanized antibody of claim 14.

16. The antibody or antigen-binding fragment thereof of claim 10, wherein the antibody or antigen-binding fragment specifically binds to the extracellular domain of Toll-like receptor-2protein (TLR2).

17. A method of inhibiting TLR2 activation in a cell, the method comprising contacting the cell with the antibody of claim 10.

18. An isolated antibody that specifically binds to Toll-like receptor-2 (TLR2) and is produced by a hybridoma cell line deposited with the American Type Culture Collection under deposit no. PAT-5014.

19. The antibody or antigen-binding fragment thereof of claim 18, wherein the antibody or antigen-binding fragment specifically binds to the extracellular domain of Toll-like receptor-2 protein (TLR2).

20. A method of inhibiting TLR2 activation in a cell, the method comprising contacting the cell with the antibody of claim 18.

21. An isolated Fab fragment of monoclonal antibody 11G7 that specifically binds to Toll-like receptor-2 protein (TLR2).

22. The isolated Fab fragment of claim 21, wherein the Fab fragment specifically binds to Toll-like receptor-2 protein (TLR2).

* * * * *